(12) United States Patent
Sanghavi et al.

(10) Patent No.: US 12,391,924 B2
(45) Date of Patent: Aug. 19, 2025

(54) METHOD FOR MESENCHYMAL STEM CELL ISOLATION AND OSTEOBLAST DIFFERENTIATION

(71) Applicant: REGROW BIOSCIENCES PRIVATE LIMITED, Mumbai (IN)

(72) Inventors: Satyen Sanghavi, Mumbai (IN); Vinayak Kedage, Pune (IN)

(73) Assignee: REGROW BIOSCIENCES PRIVATE LIMITED, Mumbai (IN)

( * ) Notice: Subject to any disclaimer, the term of this patent is extended or adjusted under 35 U.S.C. 154(b) by 973 days.

(21) Appl. No.: 17/428,587

(22) PCT Filed: Feb. 7, 2020

(86) PCT No.: PCT/IN2020/050123
§ 371 (c)(1),
(2) Date: Aug. 4, 2021

(87) PCT Pub. No.: WO2020/161748
PCT Pub. Date: Aug. 13, 2020

(65) Prior Publication Data
US 2022/0098553 A1  Mar. 31, 2022

(30) Foreign Application Priority Data
Feb. 8, 2019 (IN) .............................. 201921005151

(51) Int. Cl.
| | | |
|---|---|---|
| C12N 5/077 | (2010.01) | |
| A61K 35/32 | (2015.01) | |
| C12N 5/0775 | (2010.01) | |

(52) U.S. Cl.
CPC ............ *C12N 5/0654* (2013.01); *A61K 35/32* (2013.01); *C12N 5/0663* (2013.01); *C12N 2501/105* (2013.01); *C12N 2501/113* (2013.01); *C12N 2501/135* (2013.01); *C12N 2501/148* (2013.01); *C12N 2501/155* (2013.01); *C12N 2501/165* (2013.01); *C12N 2502/115* (2013.01); *C12N 2506/1353* (2013.01)

(58) Field of Classification Search
CPC .......... C12N 2506/1353; C12N 5/0663; A61K 35/28
See application file for complete search history.

(56) References Cited

U.S. PATENT DOCUMENTS

2007/0265558 A1   11/2007   Kleinbloesem et al.

FOREIGN PATENT DOCUMENTS

| JP | 5148873 B2 | 2/2013 |
| WO | 2005/003334 A2 | 1/2005 |
| WO | 2007/083093 A1 | 7/2007 |

OTHER PUBLICATIONS

Han YF, Tao R, Sun TJ, Chai JK, Xu G, Liu J. Optimization of human umbilical cord mesenchymal stem cell isolation and culture methods. Cytotechnology. Oct. 2013;65(5):819-27. doi: 10.1007/s10616-012-9528-0. Epub Jan. 11, 2013. PMID: 23306781; PMCID: PMC3967601. (Year: 2013).*

Doucet C, Ernou I, Zhang Y, Llense JR, Begot L, Holy X, Lataillade JJ. Platelet lysates promote mesenchymal stem cell expansion: a safety substitute for animal serum in cell-based therapy applications. J Cell Physiol. Nov. 2005;205(2):228-36. doi: 10.1002/jcp.20391. PMID: 15887229. (Year: 2005).*

Ullah I, Subbarao RB, Rho GJ. Human mesenchymal stem cells—current trends and future prospective. Biosci Rep. Apr. 28, 2015;35(2):e00191. doi: 10.1042/BSR20150025. PMID: 25797907; PMCID: PMC4413017. (Year: 2015).*

Bortolotti F, Ukovich L, Razban V, Martinelli V, Ruozi G, Pelos B, Dore F, Giacca M, Zacchigna S. In vivo therapeutic potential of mesenchymal stromal cells depends on the source and the isolation procedure. Stem Cell Reports. Mar. 10, 2015;4(3):332-9. (Year: 2015).*

Etulain J, Negrotto S, Schattner M. Role of Platelets in Angiogenesis in Health and Disease. Current Angiogenesis, 2014, 3, 48-57. (Year: 2014).*

Augello et al., "The Regulation of Differentiation in Mesenchymal Stem Cells," *Human Gene Therapy* 21:1226-1238, Oct. 2010.

Baksh et al., "Adult Mesenchymal Stem Cells: Characterization, Differentiation, and Application in Cell and Gene Therapy," *J. Cell. Mol. Med.* 8(3):301-316, Jul.-Sep. 2004.

Bertolo et al., "Comparative Characterization of Canine and Human Mesenchymal Stem Cells Derived from Bone Marrow," *International Journal of Stem Cell Research & Therapy* 2(1), Jan. 19, 2015, 6 pages.

Bobis et al., "Mesenchymal Stem Cells: Characteristics and Clinical Applications," *Folia Histochemica Et Cytobiologica* 44(4):215-230, 2006.

(Continued)

*Primary Examiner* — Christopher M Babic
*Assistant Examiner* — Qinhua Gu
(74) *Attorney, Agent, or Firm* — Seed IP Law Group LLP

(57) ABSTRACT

The present disclosure discloses a method for isolating osteoprogenitors like mesenchymal stem cells (MSCs) from clotted bone marrow and culturing with a platelet lysate obtained from a combination of discarded umbilical cord blood and maternal blood platelet-rich plasma (instead of non-human animal origin serum) and differentiating those MSCs into osteoblasts under sterile conditions for further therapeutic applications. Particularly, the present disclosure relates to a method for expansion of osteoblasts to make cell therapy products with a fixed cell dose, which are characterized and later cryopreserved for future use through its cell culture process. Further, the present disclosure relates to identifying specific gene expression from MSCs to osteoblast formation, an in-vitro differentiation process that replicates the in-vivo bone remodelling system.

20 Claims, 7 Drawing Sheets
Specification includes a Sequence Listing.

(56) References Cited

OTHER PUBLICATIONS

Chevallier et al., "Osteoblastic Differentiation of Human Mesenchymal Stem Cells with Platelet Lysate," *Biomaterials* 31(2):270-278, Jan. 2010.

Muraglia et al., "Culture Medium Supplements Derived from Human Platelet and Plasma: Cell Commitment and Proliferation Support," *Frontiers in Bioengineering and Biotechnology 5*, Article 66, Nov. 20, 2017, 15 pages.

Murphy et al., "Adult and Umbilical Cord Blood-Derived Platelet-Rich Plasma for Mesenchymal Stem Cell Proliferation, Chemotaxis, and Cryo-Preservation," *Biomaterials* 33(21):5308-5316, Jul. 2012.

Schlaefli et al., "An Enzymatic Method to Rescue Mesenchymal Stem Cells from Clotted Bone Marrow Samples," *J Vis Exp.* 98(52694), Apr. 12, 2015, 7 pages.

Ruggiu et al., The effect of Platelet Lysate on osteoblast proliferation associated with a transient increase of the inflammatory response in bone regeneration, *Biomaterials* 34(37): 9318-9330, Dec. 2013.

* cited by examiner

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Forward Primer sequence for OCT-4

<400> SEQUENCE: 1
gttgatcctc ggacctggct a                                         21

<210> SEQ ID NO 2
<211> LENGTH: 21
<212> TYPE: DNA
<213> ORGANISM: Artificial Sequence
<220> FEATURE:
<223> OTHER INFORMATION: Reverse Primer sequence for OCT-4

<400> SEQUENCE: 2
ggttgcctct cactcggttc t                                         21

<210> SEQ ID NO 3
<211> LENGTH: 23
<212> TYPE: DNA
<213> ORGANISM: Artificial Sequence
<220> FEATURE:
<223> OTHER INFORMATION: Forward Primer sequence for Nanog

<400> SEQUENCE: 3
gtcttctgct gagatgcctc aca                                       23
```

```
<210> SEQ ID NO 4
<211> LENGTH: 23
<212> TYPE: DNA
<213> ORGANISM: Artificial Sequence
<220> FEATURE:
<223> OTHER INFORMATION: Reverse Primer sequence for Nanog

<400> SEQUENCE: 4
cttctgcgtc acaccattgc tat                                              23

<210> SEQ ID NO 5
<211> LENGTH: 21
<212> TYPE: DNA
<213> ORGANISM: Artificial Sequence
<220> FEATURE:
<223> OTHER INFORMATION: Forward Primer sequence for Sox2

<400> SEQUENCE: 5
gccgagtgga aactttgtc g                                                 21

<210> SEQ ID NO 6
<211> LENGTH: 22
<212> TYPE: DNA
<213> ORGANISM: Artificial Sequence
<220> FEATURE:
<223> OTHER INFORMATION: Reverse Primer sequence for Sox2

<400> SEQUENCE: 6
gcagcgtgta cttatccttc tt                                               22

<210> SEQ ID NO 7
<211> LENGTH: 23
<212> TYPE: DNA
<213> ORGANISM: Artificial Sequence
<220> FEATURE:
<223> OTHER INFORMATION: Forward Primer sequence for ALP

<400> SEQUENCE: 7
accattccca cgtcttcaca ttt                                              23

<210> SEQ ID NO 8
<211> LENGTH: 22
<212> TYPE: DNA
<213> ORGANISM: Artificial Sequence
<220> FEATURE:
<223> OTHER INFORMATION: Reverse Primer sequence for ALP

<400> SEQUENCE: 8
agacattctc tcgttcaccg cc                                               22

<210> SEQ ID NO 9
<211> LENGTH: 24
<212> TYPE: DNA
<213> ORGANISM: Artificial Sequence
<220> FEATURE:
<223> OTHER INFORMATION: Forward Primer sequence for Collagen-1

<400> SEQUENCE: 9
ggacacaatg gattgcaagg ccgc                                             24

<210> SEQ ID NO 10
<211> LENGTH: 24
<212> TYPE: DNA
<213> ORGANISM: Artificial Sequence
<220> FEATURE:
<223> OTHER INFORMATION: Reverse Primer sequence for Collagen-1
```

```
<400> SEQUENCE: 10
taaccactgc tccactctgg atgg                                           24

<210> SEQ ID NO 11
<211> LENGTH: 23
<212> TYPE: DNA
<213> ORGANISM: Artificial Sequence
<220> FEATURE:
<223> OTHER INFORMATION: Forward Primer sequence for RunX2

<400> SEQUENCE: 11
agatgatgac actgccacct ctg                                            23

<210> SEQ ID NO 12
<211> LENGTH: 21
<212> TYPE: DNA
<213> ORGANISM: Artificial Sequence
<220> FEATURE:
<223> OTHER INFORMATION: Reverse Primer sequence for RunX2

<400> SEQUENCE: 12
gggatgaaat gcttgggaac t                                              21

<210> SEQ ID NO 13
<211> LENGTH: 26
<212> TYPE: DNA
<213> ORGANISM: Artificial Sequence
<220> FEATURE:
<223> OTHER INFORMATION: Forward Primer sequence for Osterix

<400> SEQUENCE: 13
tagtggtttg gggtttgttt taccgc                                         26

<210> SEQ ID NO 14
<211> LENGTH: 26
<212> TYPE: DNA
<213> ORGANISM: Artificial Sequence
<220> FEATURE:
<223> OTHER INFORMATION: Reverse Primer sequence for Osterix

<400> SEQUENCE: 14
aaccaactca ctcttattcc ctaagt                                         26

<210> SEQ ID NO 15
<211> LENGTH: 19
<212> TYPE: DNA
<213> ORGANISM: Artificial Sequence
<220> FEATURE:
<223> OTHER INFORMATION: Forward Primer sequence for ICAM-1

<400> SEQUENCE: 15
ggccggccag cttatacac                                                 19

<210> SEQ ID NO 16
<211> LENGTH: 20
<212> TYPE: DNA
<213> ORGANISM: Artificial Sequence
<220> FEATURE:
<223> OTHER INFORMATION: Reverse Primer sequence for ICAM-1

<400> SEQUENCE: 16
tagacacttg agctcgggca                                                20

<210> SEQ ID NO 17
```

```
<211> LENGTH: 20
<212> TYPE: DNA
<213> ORGANISM: Artificial Sequence
<220> FEATURE:
<223> OTHER INFORMATION: Forward Primer sequence for Leptin receptor

<400> SEQUENCE: 17
aggaagcccg aagttgtgtt                                              20

<210> SEQ ID NO 18
<211> LENGTH: 19
<212> TYPE: DNA
<213> ORGANISM: Artificial Sequence
<220> FEATURE:
<223> OTHER INFORMATION: Reverse Primer sequence for Leptin receptor

<400> SEQUENCE: 18
tctggtcccg tcaatctga                                               19

<210> SEQ ID NO 19
<211> LENGTH: 27
<212> TYPE: DNA
<213> ORGANISM: Artificial Sequence
<220> FEATURE:
<223> OTHER INFORMATION: Forward Primer sequence for Ephrin B2

<400> SEQUENCE: 19
gcatctgtct gcttggtctt tatcaac                                      27

<210> SEQ ID NO 20
<211> LENGTH: 21
<212> TYPE: DNA
<213> ORGANISM: Artificial Sequence
<220> FEATURE:
<223> OTHER INFORMATION: Reverse Primer sequence for Ephrin B2

<400> SEQUENCE: 20
atggctgtga gaagggactc c                                            21

<210> SEQ ID NO 21
<211> LENGTH: 25
<212> TYPE: DNA
<213> ORGANISM: Artificial Sequence
<220> FEATURE:
<223> OTHER INFORMATION: Forward Primer sequence for Ephrin B4

<400> SEQUENCE: 21
gaagaaggag agctgtgtgg caatc                                        25

<210> SEQ ID NO 22
<211> LENGTH: 24
<212> TYPE: DNA
<213> ORGANISM: Artificial Sequence
<220> FEATURE:
<223> OTHER INFORMATION: Reverse Primer sequence for Ephrin B4

<400> SEQUENCE: 22
gatgactgtg aactgtccgt cgtt                                         24

<210> SEQ ID NO 23
<211> LENGTH: 24
<212> TYPE: DNA
<213> ORGANISM: Artificial Sequence
<220> FEATURE:
<223> OTHER INFORMATION: Forward Primer sequence for MEPE

<400> SEQUENCE: 23
```

```
cgagtttttct gtgtgggact actc                                              24
```

<210> SEQ ID NO 24
<211> LENGTH: 28
<212> TYPE: DNA
<213> ORGANISM: Artificial Sequence
<220> FEATURE:
<223> OTHER INFORMATION: Reverse Primer sequence for MEPE

<400> SEQUENCE: 24

```
cttagttttc tcagtctgtg gttgaaat                                           28
```

METHOD FOR MESENCHYMAL STEM CELL ISOLATION AND OSTEOBLAST DIFFERENTIATION

STATEMENT REGARDING SEQUENCE LISTING

The Sequence Listing associated with this application is provided in text format in lieu of a paper copy, and is hereby incorporated by reference into the specification. The name of the text file containing the Sequence Listing is SEQUENCE_LISTING_790161_401USPC. The text file is 6 KB, was created on Aug. 3, 2021, and is being submitted electronically via EFS-Web.

FIELD OF INVENTION

The present disclosure relates to cell therapy, preferably cell therapy in humans, particularly isolated progenitor cells from clotted bone marrow, a method for deriving such cells, and methods to differentiate such cells in culture.

BACKGROUND OF INVENTION

In stem cell research, the regenerative properties of human mesenchymal stem cells (MSCs) from bone marrow for the cells' potential therapeutic applications is an important topic of research. MSCs are a promising source of adult stem cells for regenerative medicine, however many senescent cells are found in the heterogeneous ensemble of progenitors and lineage-committed cells that are associated with loss of proliferation potential and differentiation potential.

Regenerative properties are highly variable among MSC subsets. Consequently, identification and isolation of progenitor subsets in heterogeneous MSC cultures are essential to the development of highly efficacious stem cell therapies. In other words, the elimination of senescent cells from heterogeneous MSC cultures may improve the treatment outcome of autologous MSC therapies by increasing both cells yield and enhancing the integrity of regenerated tissue.

The bone marrow stroma was originally thought to function mainly as a structural framework for the hematopoietic component of the marrow. Subsequently, it has become well established that the stroma consists of a heterogeneous population of cells, a subset of which exerts both positive and negative regulatory effects on the proliferation and differentiation of hematopoietic stem cells (HSC) in the marrow through a combination of physical and chemical signals. The stroma also contains other non-hematopoietic cells termed mesenchymal stem cells (MSC), which are capable of both self-renewal and differentiation into osteoblasts, adipocytes, myoblasts and chondroblasts. The number of HSCs in bone marrow is about 10-100 times greater than that of MSCs. MSCs also give rise to a variety of mature cell types via a step-wise maturation process similar to haematopoiesis, termed mesengenesis. Functions that have been attributed to MSCs include, for example, the daily control of inflammation, immune response, haematopoiesis and organ integrity.

Despite the features ascribed to MSC populations by in-vitro differentiation capabilities of theirs, the mechanisms governing their proliferation and multi-lineage differentiation capacity have been poorly understood.

A current barrier to realizing the therapeutic potential of MSCs is the inability to identify different MSC populations in a heterogeneous culture. The heterogeneous cultures which include cells with lower proliferation and multipotent potential results in substantial variation and decreases the effectiveness of stem cell therapies with MSCs. Ex-vivo preparations of bone marrow aspirates can show a great diversity of cell types.

Even the so-called "pure MSC" preparations demonstrate heterogeneity with variations in therapeutic effect, potency, differentiation capacity, mitotic activity, and so forth. For example, MSCs are known to undergo phenotypic rearrangements during ex-vivo manipulations, losing expression of some markers while acquiring new ones (see Augello et al. Human Gene Therapy 21:1226-1238 (October 2010)). Depending on culture conditions, various MSC subsets are preferentially expanded in culture, differing, for example, in expression of surface markers and other proteins, differentiation capacity, proliferation, and morphology (see Baksh et al. J. Cell. Mol. Med. Vol 8, No 3, 2004 pp. 301-316; Bobis et al. Folia Histochemica Et Cytobiologica. Vol. 44, No. 4, 2006; pp. 215-230).

The art is replete with reports of poorly characterized preparations based on a mixed variety of cellular phenotypes derived from a mixed variety of manufacturing techniques. While there is a tendency among some to combine teachings from such reports, such combinations can lead to false conclusions when the reports represent different MSC populations. To advance the understanding of MSC biology and therapy, it will be important to fully characterize the phenotype of MSCs in a preparation and to recognize heterogeneity where it exists.

JP5148873B2 discloses the isolation of a homogeneous population of cells from umbilical cord tissue containing no blood, cell renewal, expansion and differentiation in culture, where one of the process steps involves the use of dispase, hyaluronidase, and collagenase for isolation of cells.

US20070265558 discloses a process for extraction and separation of bone marrow cells that enables the increase of their therapeutic potency, where the process involves the steps collection of buffy coat by centrifugation.

Schlaefli et al. (Journal of visualized experiments: JoVE, 98 52694. 12 Apr. 2015, doi:10.3791/52694), discloses that upon withdrawal, bone marrow may clot, as it comprises all of the hematopoietic system, leading to a loss of MSCs for expansion culture and direct stem cell therapy.

Muraglia et al. (Frontiers in bioengineering and biotechnology vol. 5 66. 20 Nov. 2017, doi:10.3389/fbioe.2017.00066), discloses additives which are (i) a heparin-free human platelet lysate (PL) devoid of serum or plasma components (v-PL) and (ii) a heparin-free human serum derived from plasma devoid of PL components (Pl-s) and to their use as single components or in combination in primary or cell line cultures.

Ruggiu et al. (Biomaterials, Vol. 34, No. 37, 2013; pp. 9318-9330), assesses the regenerative potential of platelet lysates for bone repair.

Thus, what is needed in the art is the ability to manufacture uniform preparations of MSCs in numbers sufficient for one or more therapeutically-effective doses, having a reproducible therapeutic action, and having a phenotype that is stable during ex-vivo expansion and following cryogenic preservation. Also required is a method of expanding and differentiating MSCs in culture under conditions that recapitulate bone remodelling in-vivo so as to reach transplantation-ready osteoblasts, for example, to treat patients with bone defects and injuries so as to repopulate, rejuvenate and fix such bone tissues.

All publications have been added fully to the disclosure by reference.

SUMMARY OF THE INVENTION

In an aspect of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature of at least 35° C. for a time of at least 20 minutes to obtain incubated clotted bone marrow reaction solution; (e) contacting the incubated clotted bone marrow reaction solution of step (d) to a growth medium to obtain a suspension; (f) mixing the suspension for a plurality of repeats; (g) filtering the suspension of step (f) with a cell strainer to obtain a filtrate; (h) centrifuging the filtrate to obtain a cell pellet; and (i) dissolving the cell pellet with a nutrient medium to obtain a mesenchymal stem cell suspension, wherein the nutrient medium comprises 5% to 20% of a platelet lysate.

In another aspect of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (e) contacting the incubated clotted bone marrow reaction solution of step (d) to a growth medium to obtain a suspension; (f) mixing the suspension for a plurality of repeats; (g) filtering the suspension of step (f) with a cell strainer with a pore size in a range of 50 μm-100 μm to obtain a filtrate; (h) centrifuging the filtrate at 1300 rpm to 1800 rpm for a time in a range of 10 minutes to 15 minutes to obtain a cell pellet; and (i) dissolving the cell pellet with a nutrient medium to obtain a mesenchymal stem cell suspension, wherein the nutrient medium comprises 5% to 20% of a platelet lysate.

In yet another aspect of the present disclosure, there is provided a method for preparing transplantation-ready osteoblast cells from mesenchymal stem cell suspension, said method comprising: (i) seeding in a culture flask, a mesenchymal stem cell suspension obtained from a process comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (e) contacting the incubated clotted bone marrow reaction solution of step (d) to a growth medium to obtain a suspension; (f) mixing the suspension for a plurality of repeats; (g) filtering the suspension of step (f) with a cell strainer with a pore size in a range of 50 μm-100 μm to obtain a filtrate; (h) centrifuging the filtrate at 1300 rpm to 1800 rpm for a time in a range of 10 minutes to 15 minutes to obtain a cell pellet; and (i) dissolving the cell pellet with a nutrient medium to obtain a mesenchymal stem cell suspension, wherein the nutrient medium comprises 5% to 20% of a platelet lysate, to obtain culture flask-adhered mesenchymal stem cells; (ii) culturing the adhered mesenchymal stem cells in a nutrient medium comprising 5% to 20% of a platelet lysate in the nutrient medium; (iii) supplementing the nutrient medium of step (ii) with differentiation factors and growth factors to obtain a differentiation medium; (iv) complementing the differentiation nutrient medium of step (iii) with fresh differentiation nutrient medium comprising 5% to 20% of a platelet lysate, differentiation factors and growth factors to obtain a population of pre-osteoblast cells; (v) sub-culturing the population of pre-osteoblast cells of step (iv) for a time in a range of 6 to 10 days to obtain a pre-osteoblast cells; and (vi) expanding the pre-osteoblast cells in an expansion nutrient medium comprising 5% to 20% of a platelet lysate, for a time in a range of 10 to 20 days to obtain transplantation-ready osteoblast cells.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

Figure 7:
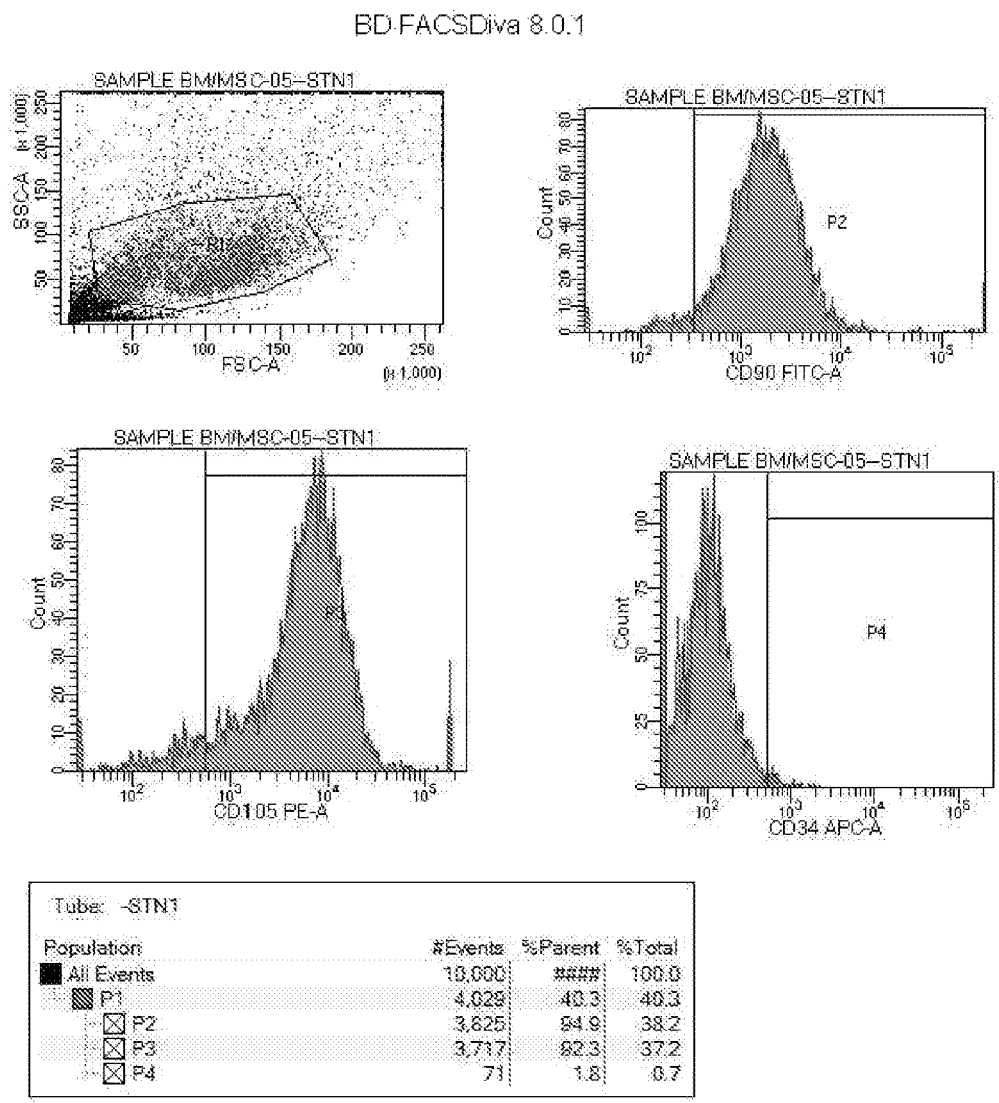

FIG. 7 illustrates demonstrates representative FACS data that shows immunophenotypic results using flow cytometry for bone marrow derived MSCs at 14±3 days of culture for CD90, CD105 positive expression and CD34 negative expression, in accordance with an embodiment of the present disclosure. P1 depicts forward scattering v/s side scattering data, P2 with FITC depicts results for CD90, P3 with PE depicts results for CD105, and P4 with APC depicts results for CD34.

Figure 8:
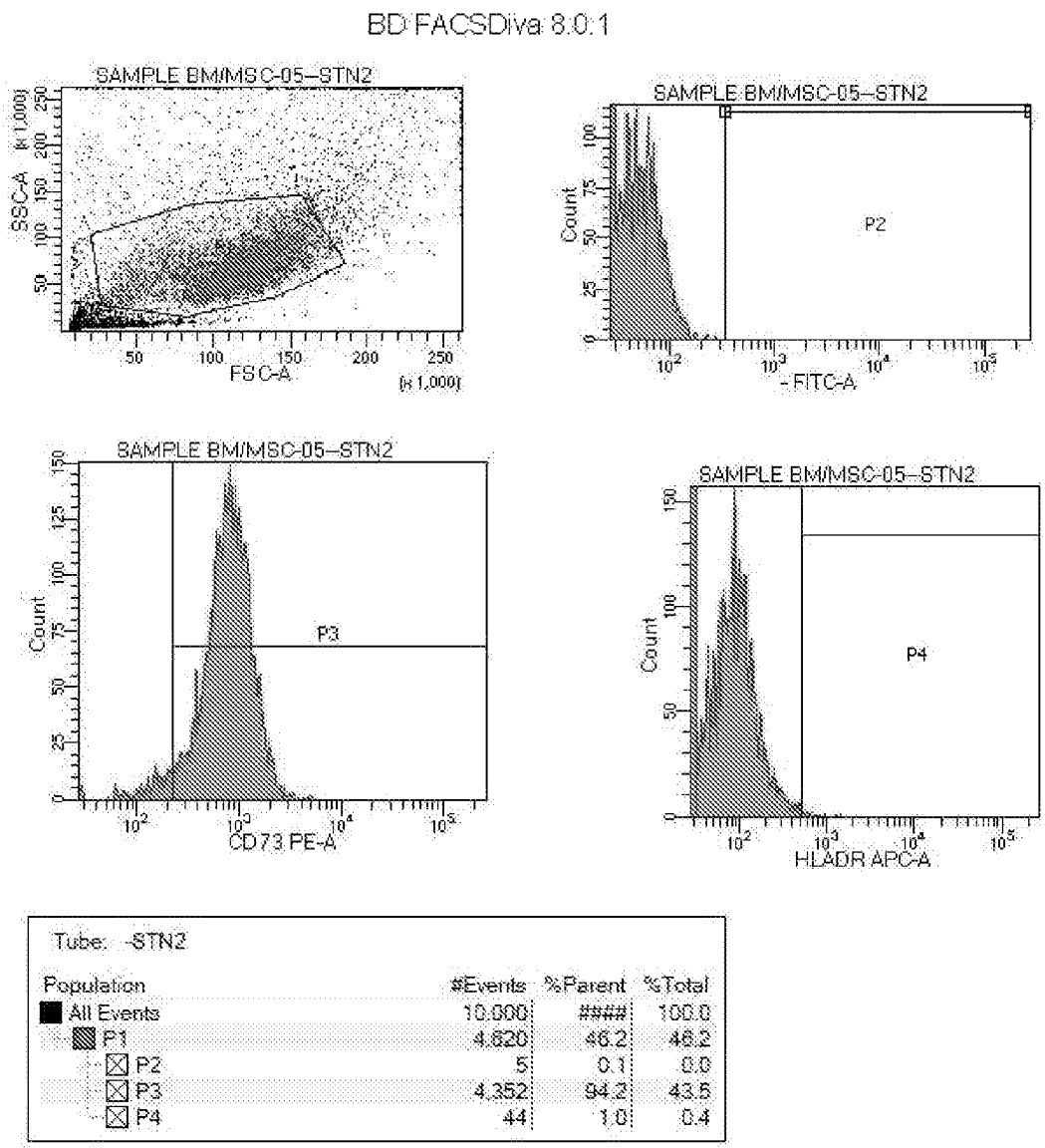

FIG. 8 illustrates representative FACS data that shows immunophenotypic results using flow cytometry for bone marrow derived MSCs at 14±3 days of culture for CD73 positive expression and HLA-DR negative expression, in accordance with an embodiment of the present disclosure. P1 depicts forward scattering v/s side scattering data, P2 with FITC does not gate for any marker, P3 with PE depicts results for CD73, and P4 with APC depicts results for HLA-DR.

Figure 9:
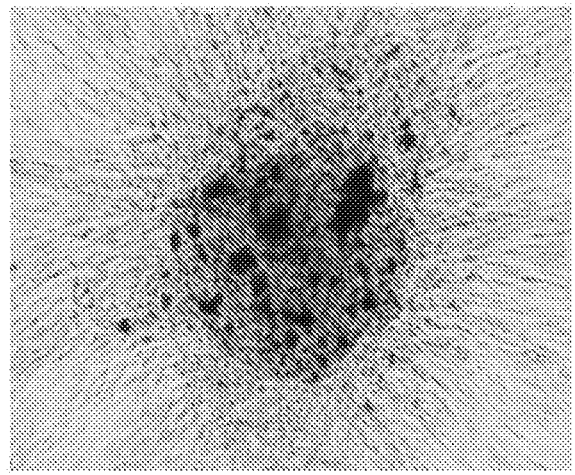

FIG. 9 illustrates a representative image of stained calcified nodules, i.e., final product of cultured osteoblast cells in the culture using Alizarin red mineralization stain, which were taken under 100× of inverted microscope, in accordance with an embodiment of the present disclosure.

Figure 10:
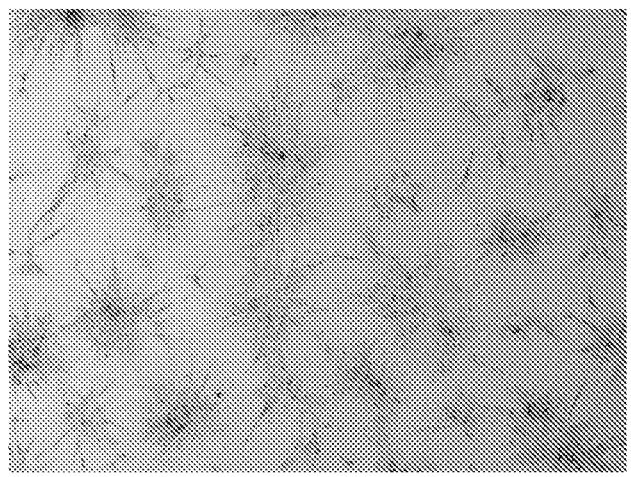

FIG. 10 illustrates a representative image of stained calcified nodules, i.e., final product of cultured osteoblast cells in the culture using Alizarin red mineralization stain, which were taken under 40× of inverted microscope, in accordance with an embodiment of the present disclosure.

Figure 11:
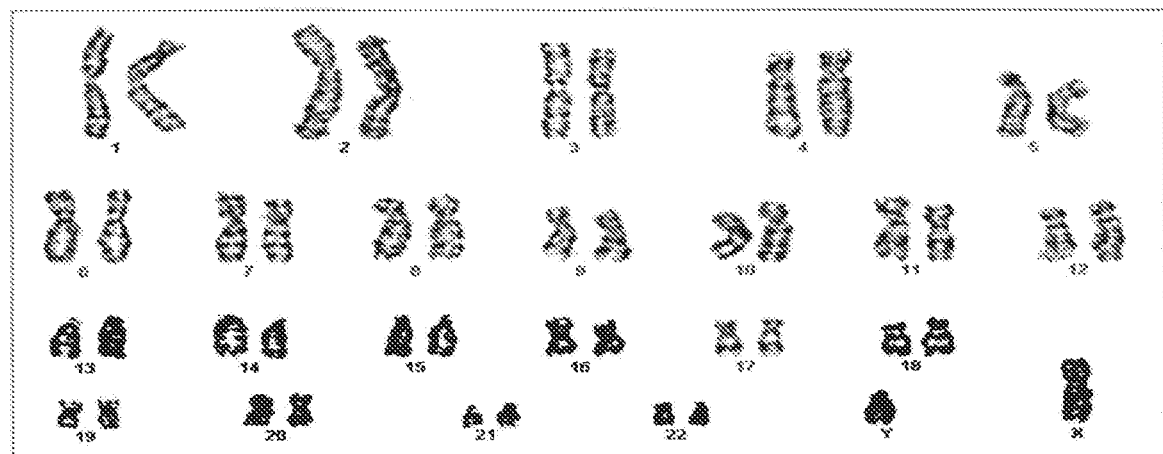

FIG. 11 illustrates a representative karyotyping analysis of final product of cultured osteoblasts cells, in accordance with an embodiment of the present disclosure.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Sequences 1 to 24 as disclosed herein (see Table 10) have been provided as a computer readable text file.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "clotted bone marrow" as used herein means harvested bone marrow from clotting due to coagulation.

The term "buffer" as used herein means solution to maintain stable pH in the solution as they can neutralize small quantities of additional acid or base.

The term "at least" as used herein means not less than the following amount.

The term "lysate" as used herein includes cellular lysates, platelet lysates, plasma and combinations thereof that are procured following cellular lysis. Cellular lysis may be brought on by freeze/thaw cycles, osmotic changes, other physical and chemical means known in the field.

The term "platelet-rich plasma" (PRP) as used herein means the less light plasma portion of the blood that comprises platelets in a concentration above one million per microliter.

The term "platelet lysate" as used herein means cell lysates produced from regular platelet transfusion units by lysis.

The term "platelet" as used herein refers to cells which are small a-nucleated structures of hematopoietic origin which contribute to homeostasis and wound healing by secreting growth factors and cytokines. They are produced by the fragmentation of megakaryocytes and released into the bloodstream, where they circulate for 7-10 days before being replaced.

The term "umbilical cord blood" (UCB) as used herein means the blood that remains in the placenta and in the attached umbilical cord after childbirth. Cord blood is collected because it contains stem cells, which can be used to treat hematopoietic and genetic disorders. Generally, a lot of this rich biological resource is discarded. The preferred source is human.

The process for umbilical cord blood (UCB) collection entails: (a) confirming the identity of a subject, (b) cleaning the segment of the umbilical cord with 10% povidone Iodine and 70% alcohol (Ethyl Alcohol/Isopropyl Alcohol) thrice alternately, swabbing away from the collection area, before collection, (c) after spirit evaporates, removing outer gloves to prevent contamination, (d) holding cord blood collection bag with sterile inner gloves, (e) inserting one end of a needle in the umbilical cord vein near the cord clamp and the other end into a blood collection bag, (f) gently and properly mixing the cord blood flowing into the collection bag with an anticoagulant, (g) once umbilical cord appears empty and whitish and all blood has been removed, stopping the blood link through the needle, checking for leakage, if any, and cleaning the blood collection bag with the collected umbilical cord blood (UCB) with sterile gauze. The preferred source is human.

The term "maternal blood" (MB) as used herein means the blood collected from a mother pre- and post-delivery. The maternal blood (MB) collection may take place at a time immediately before/after cord blood collection, at the time of admission for delivery (after initiation of labour) or before transfusion/infusion of any intravenous fluid (colloids/crystalloids/blood products). The preferred source is human.

The term "umbilical cord blood and maternal blood" (UCB+MB) as used herein means any combination of an umbilical cord blood and maternal blood. Said combination may come from autologous and/or allogenic sources. The preferred source is human.

The term "a combination of umbilical cord blood derived platelets and maternal blood derived platelets" as used herein refers to mixing or combination of platelets derived from processing umbilical cord blood and maternal blood, whether allogenous or autogenous by origin, and mixed in a ratio in a range of 10:1 to 30:1, preferably, 10:1 to 26:1.

The MSCs may be from an autologous or allogenous source, where the source is human for another subject human.

The term "transplantation-ready" as used herein refers to mature osteoblast cells that need not undergo any further expansion and are ready to be transplanted into a subject in need. Further, the cell number for such transplantation-ready osteoblasts are determined based on the size and characteristics of the site of transplant. The term "heat shock proteins" or "HSP" is intended to cover all the heat shock proteins that is known in the art ranging from 10-100 kDa. HSP 70 is one such heat shock protein with 70 kDa molecular weight.

Abbreviations as used herein include, α-MEM—α Minimum Essential Medium, DMEM—Dulbecco's Modified Eagle Medium, IMDM—Iscove's Modified Dulbecco's Medium, EMEM—Eagle's Minimum Essential Medium, FGF—Fibroblast Growth Factor, TGF—Transforming Growth Factor, IGF—Insulin-like growth factor 1, VEGF—Vascular endothelial growth factor, PDGF—Platelet-derived growth factor, BMP-2—Bone Morphogenic Protein-2, CD90—Cluster of Differentiation 90, CD73—Cluster of Differentiation 73, CD105—Cluster of Differentiation 105, CD34—Cluster of Differentiation 34, HLA-DR—Human Leukocyte Antigen—DR isotype, umbilical cord blood (UCB), maternal blood (MB), platelet-rich plasma (PRP), platelet lysate (PL), mesenchymal stem cells (MSCs), OCT-4—octamer-binding transcription factor 4, Sox-2—Sex determining region Y box 2, ALP—Alkaline phosphatase, bone alkaline phosphatase.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

To address the problems encountered as discussed above, while isolating and culturing mammalian or human (primary) mesenchymal stem cells and their differentiation to osteoblastic cells in the presence of optimized media composition demonstrated results in terms of enhanced expansion and the formation of aggregates or clusters of mesenchymal stem cells or of osteoblastic cells evenly distributed in the culture medium which is ultimately useful for therapeutic applications. The present disclosure provides a method that is applicable for both allogenous and autogenous sources of osteoprogenitors.

In particular, the present disclosure is based on the insight that culturing human or mammalian mesenchymal stem cells or osteoblastic cells in the presence of an optimized media composition derivative over a restricted period of time, such as over two weeks or less, in particular over a time of one week or less, allows to obtain aggregates or clusters of osteoblastic cells having a unique cell count.

More particularly, the present disclosure is believed to be more advantageous over the conventional technique of producing pure osteoblastic culture, i.e., delay in the transformation of osteoblastic cell aggregates to osteocyte aggregates, that is, the mineralization of the osteoblastic cell aggregates in-vitro and in-vivo in the presence of optimized culture media of appropriate kind.

The present disclosure relates to: a method of preparing an osteoblast from an MSCs population of a mammal, the method including, enzymatic and mechanical chopping of the subject sample introducing enzyme combination with sets of different media composition for differentiation or expansion or proliferation of osteoblast or osteoprogenitors thereof mimicking in-vivo bone remodeling system through the expression of genetic markers independently into the cell, the bone-related genes including, at least one kind selected from the group consisting of OCT-4, Nanog, Sox2, ALP, Collagen-1, RunX2, Ephrin B4, Osterix, MEPE, ICAM-1, Leptin receptor, Ephrin B2 and an osteoblast prepared by the method.

Further, it is observed that in the presence of the optimized media derivative of the invention, the process enhances cell proliferation even more; concomitantly inducing the expression of osteoblastic cell markers, indicative of differentiation towards mature osteoblasts in the respective cell culture medium. The present invention allows to obtain such cell aggregates faster and in substantially greater amounts than by known culturing processes.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 $mm^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature of at least 35° C. for a time of at least 20 minutes to obtain incubated clotted bone marrow reaction solution; (e) contacting the incubated clotted bone marrow reaction solution of step (d) to a growth medium to obtain a suspension; (f) mixing the suspension for a plurality of repeats; (g) filtering the suspension of step (f) with a cell strainer to obtain a filtrate; (h) centrifuging the filtrate to obtain a cell pellet; and (i) dissolving the cell pellet with a nutrient medium to obtain a mesenchymal stem cell suspension, wherein the nutrient medium comprises 5% to 20% of a platelet lysate. In another embodiment of the present disclosure as described herein, chopping the clotted bone marrow is done into pieces having size in a range of 2-5 $mm^3$, or 2-3 $mm^3$, incubating the clotted bone marrow solution is done at a temperature in a range of 35-39° C., for a time in a range of 20-30 minutes, and at a speed in a range of 100-200 rpm, and the cell strainer has a pore size in a range of 50-100 μm, centrifuging the filtrate is done at a speed in a range of 1300-1800 rpm for a time in a range of 10-15 minutes, and the at least one enzyme is selected from a group consisting of urokinase, collagenase, hyaluronidase, and combinations thereof, and the at least one protein is heat shock protein 70 (HSP 70). In yet another embodiment of the present disclosure as described herein, urokinase is present in a range of 10,000 units to 30,000 units, collagenase type I-II is present in a range of 200 units to 500 units, hyaluronidase type I-IV is present in a range of 200 units to 1000 units, and HSP 70 is present in a range of 100 ng/ml to 1 µg/ml. In yet another embodiment, combination of urokinase, collagenase, and hyaluronidase is used for contacting the chopped clotted bone marrow. In an alternate embodiment, combination of urokinase, collagenase, hyaluronidase, and HSP 70 is used for contacting the chopped clotted bone marrow.

In an embodiment of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (e) contacting the incubated clotted bone marrow reaction solution of step (d) to a growth medium to obtain a suspension, wherein the growth medium; (f) mixing the suspension for a plurality of repeats; (g) filtering the suspension of step (f) with a cell strainer with a pore size in a range of 50 µm-100 µm to obtain a filtrate; (g) centrifuging the filtrate at 1300 rpm to 1800 rpm for a time in a range of 10 minutes to 15 minutes to obtain a cell pellet; and (h) dissolving the cell pellet with a nutrient medium to obtain a mesenchymal stem cell suspension, wherein the nutrient medium comprises 5% to 20% of a platelet lysate, and wherein the growth medium is selected from a group consisting of α-MEM, DMEM, IMDM, F12, EMEM and combinations thereof. In another embodiment of the present disclosure as described herein, the growth medium further comprises a plurality of factors selected from a group consisting of, FGF, TGF, IGF, VEGF, PDGF, IGF, BMP-2, and combinations thereof.

In an embodiment of the present disclosure, there is provided a method for preparing mesenchymal stem cells suspension from a clotted bone marrow as described herein, wherein the growth medium is selected from a group consisting of α-MEM, DMEM, IMDM, F12, EMEM and combinations thereof, and wherein the growth medium further comprises a plurality of factors selected from a group consisting of, FGF, TGF, IGF, VEGF, PDGF, IGF, BMP-2, and combinations thereof.

In an embodiment of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (e) contacting the incubated clotted bone marrow reaction solution of step (d) to a growth medium to obtain a suspension, wherein the growth medium; (f) mixing the suspension for a plurality of repeats; (g) filtering the suspension of step (f) with a cell strainer with a pore size in a range of 50 µm-100 µm to obtain a filtrate; (g) centrifuging the filtrate at 1300 rpm to 1800 rpm for a time in a range of 10 minutes to 15 minutes to obtain a cell pellet; and (h) dissolving the cell pellet with a nutrient medium to obtain a mesenchymal stem cell suspension, wherein the nutrient medium comprises 5% to 20% of a platelet lysate, and wherein the growth medium is selected from a group consisting of α-MEM, DMEM, IMDM, F12, EMEM and combinations thereof, and wherein the nutrient medium comprises a medium selected from a group consisting of α-MEM, DMEM, IMDM, F12, EMEM and combinations thereof, and a plurality of factors selected from a group consisting of, FGF, TGF, IGF, VEGF, PDGF, IGF, BMP-2, and combinations thereof.

In an embodiment of the present disclosure, there is provided a method for preparing mesenchymal stem cells suspension from a clotted bone marrow as described herein, wherein the mesenchymal stem cell suspension comprises mesenchymal stem cells which are culture flask-adherent and stained with crystal violet stain.

In an embodiment of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme, or at least one protein, or combinations thereof in presence of a buffer to obtain a clotted bone marrow reaction solution; (d) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (e) contacting the incubated clotted bone marrow reaction solution of step (d) to a growth medium to obtain a suspension, wherein the growth medium; (f) mixing the suspension for a plurality of repeats; (g) filtering the suspension of step (f) with a cell strainer with a pore size in a range of 50 µm-100 µm to obtain a filtrate; (g) centrifuging the filtrate at 1300 rpm to 1800 rpm for a time in a range of 10 minutes to 15 minutes to obtain a cell pellet; and (h) dissolving the cell pellet with a nutrient medium to obtain a mesenchymal stem cell suspension, wherein the nutrient medium comprises 5% to 20% of a platelet lysate, and wherein the mesenchymal stem cell suspension comprises mesenchymal stem cells which test positive in flow cytometry cell surface marker analysis for CD90, CD73 and CD105, and negative for CD34 and HLA-DR.

In an embodiment of the present disclosure, there is provided a method for preparing mesenchymal stem cells suspension from a clotted bone marrow, said method comprising: (a) obtaining a bone marrow sample, wherein the bone marrow sample comprises clotted bone marrow; (b) chopping the clotted bone marrow into pieces of at least 2 mm$^3$ to obtain chopped clotted bone marrow; (c) contacting the chopped clotted bone marrow to at least one enzyme in presence of a buffer to obtain a clotted bone marrow reaction solution; (d) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (e) contacting the incubated clotted bone marrow reaction solution of step (d) to a growth medium to obtain a suspension, wherein the growth medium; (f) mixing the suspension for a plurality of repeats; (g) filtering the suspension of step (f) with a cell strainer with a pore size in a range of 50 μm-100 μm to obtain a filtrate; (g) centrifuging the filtrate at 1300 rpm to 1800 rpm for a time in a range of 10 minutes to 15 minutes to obtain a cell pellet; and (h) dissolving the cell pellet with a nutrient medium to obtain a mesenchymal stem cell suspension, wherein the nutrient medium comprises 5% to 20% of a platelet lysate, and wherein the platelet lysate comprises a lysate obtained from a mixture of an umbilical cord blood (UCB) derived platelet-rich plasma and a maternal blood (MB) derived platelet-rich plasma. In another embodiment of the present disclosure, there is provided a method for preparing mesenchymal stem cells suspension from a clotted bone marrow as described herein, wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml, or $0.3 \times 10^9$ to $0.7 \times 10^9$ platelets/ml, or $0.3 \times 10^9$ to $0.5 \times 10^9$ platelets/ml.

In an embodiment of the present disclosure, there is provided a method for preparing mesenchymal stem cells suspension from a clotted bone marrow as described herein, wherein the at least one enzyme is selected from a group consisting of urokinase, collagenase, hyaluronidase, and combinations thereof, and the at least one protein is heat shock protein (HSP 70), and urokinase is present in a range of 10,000 units to 30,000 units, collagenase type I-II is present in a range of 200 units to 500 units, hyaluronidase type I-IV is present in a range of 200 units to 1000 units, and HSP 70 is present in a range of 100 ng/ml to 1 μg/ml, and wherein the platelet lysate comprises a lysate obtained from a mixture of an umbilical cord blood (UCB) derived platelet-rich plasma and a maternal blood (MB) derived platelet-rich plasma and wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml.

In an embodiment of the present disclosure, there is provided a method for preparing mesenchymal stem cells suspension from a clotted bone marrow as described herein, wherein the growth medium is selected from a group consisting of α-MEM, DMEM, IMDM, F12, EMEM and combinations thereof, and wherein the platelet lysate comprises a lysate obtained from a mixture of an umbilical cord blood (UCB) derived platelet-rich plasma and a maternal blood (MB) derived platelet-rich plasma and wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml.

In an embodiment of the present disclosure, there is provided a method for preparing mesenchymal stem cells suspension from a clotted bone marrow as described herein, wherein the growth medium is selected from a group consisting of α-MEM, DMEM, IMDM, F12, EMEM and combinations thereof, and wherein the nutrient medium comprises a medium selected from a group consisting of α-MEM, DMEM, IMDM, F12, EMEM and combinations thereof, and a plurality of factors selected from a group consisting of, FGF, TGF, IGF, VEGF, PDGF, IGF, BMP-2, and combinations thereof, and wherein the platelet lysate comprises a lysate obtained from a mixture of an umbilical cord blood (UCB) derived platelet-rich plasma and a maternal blood (MB) derived platelet-rich plasma, and wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml.

In an embodiment of the present disclosure, there is provided a method for preparing mesenchymal stem cells suspension from a clotted bone marrow as described herein, wherein the mesenchymal stem cell suspension comprises mesenchymal stem cells which are culture flask-adherent and stained with crystal violet stain, and wherein the platelet lysate comprises a lysate obtained from a mixture of an umbilical cord blood (UCB) derived platelet-rich plasma and a maternal blood (MB) derived platelet-rich plasma, and wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; and (f) expanding the pre-osteoblast cells in an expansion nutrient medium comprising 5% to 20% of a platelet lysate, for a time in a range of 10 to 20 days to obtain transplantation-ready osteoblast cells.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method for preparing mesenchymal stem cells suspension from a clotted bone marrow, said method comprising: (i) obtaining a bone marrow sample, wherein the bone marrow sample comprises clotted bone marrow; (ii) chopping the clotted bone marrow into pieces of at least 2 mm³ to obtain chopped clotted bone marrow; (iii) contacting the chopped clotted bone marrow to at least one enzyme, or at least one protein, or combinations thereof in presence of a buffer to obtain a clotted bone marrow reaction solution; (iv) incubating the clotted bone marrow reaction solution at a temperature in a range of 35° C. to 39° C. for a time of at least 20 minutes at a speed in a range of 100 rpm to 200 rpm to obtain incubated clotted bone marrow reaction solution; (v) contacting the incubated clotted bone marrow reaction solution of step (iv) to a growth medium to obtain a suspension; (vi) mixing the suspension for a plurality of repeats; (vii) filtering the suspension of step (vi) with a cell strainer with a pore size in a range of 50 μm-100 μm to obtain a filtrate; (viii) centrifuging the filtrate at 1300 rpm to 1800 rpm for a time in a range of 10 minutes to 15 minutes to obtain a cell pellet; and (ix) dissolving the cell pellet with a nutrient medium to obtain a mesenchymal stem cell suspension, wherein the nutrient medium comprises 5% to 20% of a platelet lysate, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; and (f) expanding the pre-osteoblast cells in an expansion nutrient medium comprising 5% to 20% of a platelet lysate, for a time in a range of 10 to 20 days to obtain transplantation-ready osteoblast cells.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof; and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof. In another embodiment of the present disclosure, the differentiation medium comprises a medium selected from a group consisting of α-MEM, IMDM, and combinations thereof, and the differentiation medium comprises plurality of factors selected from a group consisting of FGF, TFG, IFG, L-Thyroxine, Calcitrol, Stanozolol, Dexamethasone, and combinations thereof.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof. In another embodiment of the present disclosure, the differentiation medium comprises a medium selected from a group consisting of α-MEM, IMDM, and combinations thereof, and the differentiation medium comprises plurality of factors selected from a group consisting of FGF, TFG, IFG, L-Thyroxine, Calcitrol, Stanozolol, Dexamethasone, and combinations thereof.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein the expansion medium comprises a medium selected from a group consisting of α-MEM, DMEM, IMDM, F12, EMEM and combinations thereof; and a plurality of factors selected from a group consisting of Geinstein, FGF, TGF, IGF, VEGF, PDGF, BMP-2, and combinations thereof.

In an embodiment of the present disclosure, there is provided a method for preparing transplantation-ready osteoblast cells from mesenchymal stem cell suspension as described herein, wherein the mesenchymal stem cell suspension comprises mesenchymal stem cells which are culture flask-adherent and stain with crystal violet stain.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the mesenchymal stem cell suspension comprises mesenchymal stem cells which are culture flask-adherent and stain with crystal violet stain.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein the mesenchymal stem cells are culture flask-adherent and stain with crystal violet stain.

In an embodiment of the present disclosure, there is provided a method for preparing transplantation-ready osteoblast cells from mesenchymal stem cell suspension as described herein, wherein the mesenchymal stem cells are culture flask-adherent and stain with crystal violet stain, and wherein the mesenchymal stem cells test positive in flow cytometry cell surface marker analysis for CD90, CD73 and CD105, and negative for CD34 and HLA-DR.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the expansion medium comprises a medium selected from a group consisting of α-MEM, DMEM, IMDM, F12, EMEM and combinations thereof; and a plurality of factors selected from a group consisting of Genistein, FGF, TGF, IGF, VEGF, PDGF, BMP-2, and combinations thereof, and wherein the mesenchymal stem cells are culture flask-adherent and stain with crystal violet stain, and wherein the mesenchymal stem cells test positive in flow cytometry cell surface marker analysis for CD90, CD73 and CD105, and negative for CD34 and HLA-DR.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein the expansion medium comprises a medium selected from a group consisting of α-MEM, DMEM, IMDM, F12, EMEM and combinations thereof; and a plurality of factors selected from a group consisting of Genistein, FGF, TGF, IGF, VEGF, PDGF, BMP-2, and combinations thereof, and wherein the mesenchymal stem cells are culture flask-adherent and stain with crystal violet stain, and wherein the mesenchymal stem cells test positive in flow cytometry cell surface marker analysis for CD90, CD73 and CD105, and negative for CD34 and HLA-DR.

In an embodiment of the present disclosure, there is provided a method for preparing transplantation-ready osteoblast cells from mesenchymal stem cell suspension, as described herein, wherein the mesenchymal stem cells are culture flask-adherent and stain with crystal violet stain, and wherein the mesenchymal stem cells test positive in flow cytometry cell surface marker analysis for CD90, CD73 and CD105, and negative for CD34 and HLA-DR, and wherein the mesenchymal stem cells test positive for OCT-4, Nanog, and Sox-2 markers in RT-PCR analysis.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the mesenchymal stem cells are culture flask-adherent and stain with crystal violet stain, and wherein the mesenchymal stem cells test positive in flow cytometry cell surface marker analysis for CD90, CD73 and CD105, and negative for CD34 and HLA-DR, and wherein the mesenchymal stem cells test positive for OCT-4, Nanog, and Sox-2 markers in RT-PCR analysis.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the expansion medium comprises a medium selected from a group consisting of α-MEM, DMEM, IMDM, F12, EMEM and combinations thereof; and a plurality of factors selected from a group consisting of Genistein, FGF, TGF, IGF, VEGF, PDGF, BMP-2, and combinations thereof, and wherein the mesenchymal stem cells are culture flask-adherent and stain with crystal violet stain, and wherein the mesenchymal stem cells test positive in flow cytometry cell surface marker analysis for CD90, CD73 and CD105, and negative for CD34 and HLA-DR, and wherein the mesenchymal stem cells test positive for OCT-4, Nanog, and Sox-2 markers in RT-PCR analysis.

In an embodiment of the present disclosure, there is provided a method for preparing transplantation-ready osteoblast cells from mesenchymal stem cell suspension as described herein, wherein the pre-osteoblast cells test positive in flow cytometry cell surface marker analysis for bone ALP. In another embodiment of the present disclosure, the pre-osteoblast cells test positive for at least one marker selected from a group consisting of ALP, collagen-1, osterix, runx2, and ephrinB4 markers, and negative for Ephrin-b2 marker in RT-PCR analysis. In yet another embodiment of the present disclosure, the pre-osteoblast cells test positive for bone ALP by histochemical analysis.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein the pre-osteoblast cells test positive in flow cytometry cell surface marker analysis for bone ALP.

In an embodiment of the present disclosure, there is provided a method for preparing transplantation-ready osteoblast cells from mesenchymal stem cell suspension as described herein, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein pre-osteoblast cells test positive for at least one marker selected from a group consisting of ALP, collagen-1, osterix, runx2, and ephrinB4 markers, and negative for Ephrin-b2 marker in RT-PCR analysis.

In an embodiment of the present disclosure, there is provided a method for preparing transplantation-ready osteoblast cells from mesenchymal stem cell suspension as described herein, wherein the transplantation-ready osteoblast cells test positive in flow cytometry cell surface marker analysis for ALP. In another embodiment of the present disclosure, there is provided a method for preparing mesenchymal stem cells suspension from a clotted bone marrow as described herein, the transplantation-ready osteoblast cells test positive for alizarin red staining. In yet another embodiment, the transplantation-ready osteoblast cells test positive for at least one marker selected from a group consisting of bone ALP, collagen-1, osterix, runx2 and ephrinB4 markers, and negative for Ephrin-b2 in RT-PCR analysis.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the transplantation-ready osteoblast cells are in a range of $12\times10^6$ cells to $60\times10^6$ cells. In another embodiment of the present disclosure, the transplantation-ready osteoblast cells are in a range of $48\times10^6$ cells to $60\times10^6$ cells. In yet another embodiment of the present disclosure, the transplantation-ready osteoblast cells are not less than $48\times10^6$ cells.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b)

with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the platelet lysate comprises a lysate obtained from a mixture of an umbilical cord blood (UCB) derived platelet-rich plasma and a maternal blood (MB) derived platelet-rich plasma. In another embodiment of the present disclosure, the mixture of an umbilical cord blood (UCB) derived platelet-rich plasma and a maternal blood (MB) derived platelet-rich plasma comprises $0.3 \times 10^9$ to $1.5 \times 10^9$ platelets/ml. In yet another embodiment of the present disclosure, the mixture of an umbilical cord blood (UCB) derived platelet-rich plasma and a maternal blood (MB) derived platelet-rich plasma comprises $0.3 \times 10^9$ to $0.7 \times 10^9$ platelets/ml. In an alternate embodiment of the present disclosure, the mixture of an umbilical cord blood (UCB) derived platelet-rich plasma and a maternal blood (MB) derived platelet-rich plasma comprises $0.3 \times 10^9$ to $0.5 \times 10^9$ platelets/ml.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein the transplantation-ready osteoblast cells are in a range of $12 \times 10^6$ cells to $60 \times 10^6$ cells. In another embodiment of the present disclosure, the transplantation-ready osteoblast cells are in a range of $48 \times 10^6$ cells to $60 \times 10^6$ cells. In yet another embodiment of the present disclosure, the transplantation-ready osteoblast cells are not less than $48 \times 10^6$ cells.

In an embodiment of the present disclosure, there is provided a method for preparing transplantation-ready osteoblast cells from mesenchymal stem cell suspension, said method comprising: (a) seeding in a culture flask, a mesenchymal stem cell suspension obtained from a method as described herein, in a nutrient medium comprising 5% to 20% of a platelet lysate in the nutrient medium, to obtain culture flask-adhered mesenchymal stem cells; (b) culturing the adhered mesenchymal stem cells in a nutrient medium comprising 5% to 20% of a platelet lysate in the nutrient medium; (c) supplementing the nutrient medium of step (b) with differentiation factors and growth factors to obtain a differentiation medium; (d) complementing the differentiation nutrient medium of step (c) with fresh differentiation nutrient medium comprising 5% to 20% of a platelet lysate, differentiation factors and growth factors to obtain a population of pre-osteoblast cells; (e) sub-culturing the population of pre-osteoblast cells of step (d) for a time in a range of 6 to 10 days to obtain a pre-osteoblast cells; (f) expanding the pre-osteoblast cells in an expansion nutrient medium comprising 5% to 20% of a platelet lysate, for a time in a range of 10 to 20 days to obtain transplantation-ready osteoblast cells, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of, FGF, TGF, VEGF, PDGF, IGF, BMP-2, and combinations thereof, and wherein the differentiation medium comprises a medium selected from a group consisting of α-MEM, DMEM, IMDM, F12, EMEM and combinations thereof; and a plurality of factors selected from a group consisting of, FGF, TGF, IGF, VEGF, PDGF, BMP-2 L-Thyroxine, Calcitrol, Stanozolol, Dexamethasone, β-glycerophosphate, L-Ascorbic acid, and combinations thereof, and wherein the platelet lysate comprises a lysate obtained from a mixture of an umbilical cord blood (UCB) derived platelet-rich plasma and a maternal blood (MB) derived platelet-rich plasma. In another embodiment of the present disclosure, the mixture of an umbilical cord blood (UCB) derived platelet-rich plasma and a maternal blood (MB) derived platelet-rich plasma comprises $0.3 \times 10^9$ to $1.5 \times 10^9$ platelets/ml. In yet another embodiment of the present disclosure, the mixture of an umbilical cord blood (UCB) derived platelet-rich plasma and a maternal blood (MB) derived platelet-rich plasma comprises $0.3 \times 10^9$ to $0.7 \times 10^9$ platelets/ml. In an alternate embodiment of the present disclosure, the mixture of an umbilical cord blood (UCB) derived platelet-rich plasma and a maternal blood (MB) derived platelet-rich plasma comprises $0.3 \times 10^9$ to $0.5 \times 10^9$ platelets/ml.

Although the subject matter has been described in considerable detail with reference to certain examples and implementations thereof, other implementations are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

The examples as presented herein describe the best working process of the present disclosure.

Example 1

Collection of Biopsies

Patient enrolled for biopsy who had undergone the required physical and medical examination and found fit therefrom, was selected for bone therapy. Patient under medical supervision of surgeon and under required hospital conditions underwent biopsy collection under anaesthetic conditions. Using Jamshidi needle, 5 ml of bone marrow biopsy from iliac crest/sternum of patient was collected in transport medium containing 90% α-MEM with 10% platelet lysate (PL) or 10% FBS. The collected sample properly labelled and packed and details of the patient recorded in biopsy collection form. The collected sample also had 100-1000 units of heparin per 10 ml of transport medium containing in one 25 ml transport container. Several factors including and not limited to improper collection of bone marrow, improper mixing of bone marrow with transport medium, deviation in temperature during transportation or any others affects the quality of the sample.

Example 2

Transportation:

The transportation kit was validated at different temperatures before collecting the bone marrow biopsy such as 2-8° C. for a minimum of 72 hours before transportation of actual biopsy sample. The collected bone marrow biopsy along with patient details was transported in transport kit box under controlled temperature (2-8° C.) to processing facility precaution has been taken that sample should reached and processed before 72 hours from the time if collection.

Example 3

Figure 1:
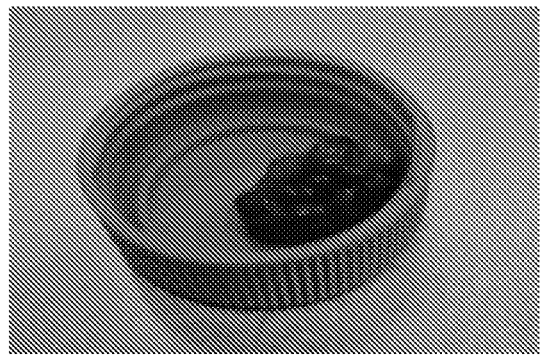
FIG. 1 illustrates a representative clotted bone marrow biopsy, in accordance with an embodiment of the present disclosure.
Figure 2:
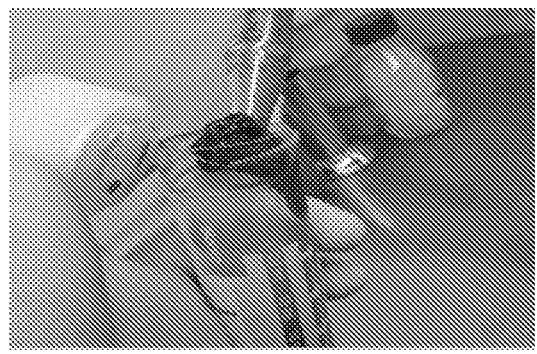
FIG. 2 illustrates a representative pipetting bone marrow biopsy, in accordance with an embodiment of the present disclosure.
Figure 3:
FIG. 3 illustrates a representative sample that was filtered with 100 μM cell strainer, in accordance with an embodiment of the present disclosure.

Isolation of Osteoprogenitor/MSCS from Clotted Bone Marrow:

Bone marrow biopsy was collected in transport vial containing transport medium (90% α-MEM+10% (UCB+MB) PL). The "PL" mentioned in the examples section refer to the platelet lysate comprising a lysate obtained from a mixture of an umbilical cord blood (UCB) derived platelet-rich plasma and a maternal blood (MB) derived platelet-rich plasma, wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml. Clot formation was due to proteins in the blood and platelets of bone marrow sample and improper mixing of bone marrow. The clotted bone marrow sample (see FIGS. 1 and 2) was not suitable for isolation of osteoprogenitor cells/MSCs and would have resulted in discarding of the bone marrow sample. To overcome this problem clotted bone marrow sample was placed on 100 μm cell strainer (see FIG. 3) on top of a sterile 50 ml centrifuge tube. Carefully the bone marrow aspirate was transferred from the transport kit onto the cell strainer, tilting the strainer or moving around the clot, using a sterile pipet tip for better flow through the filter mesh. Clotted bone marrow which was collected on cell strainer was then taken into an empty cell culture Petri dish using sterile forceps. Clot was chopped into small pieces of approximately 2-3 mm$^3$ using a sterile scalpel and sterile needle. Small pieces of the clot were then transferred into a 50 ml centrifuge tube using the sterile forceps.

By Using Enzymatic Method Along with Above Chopping Method: Part of Isolation

To the above-mentioned small chopped pieces of bone clots, 10 ml of freshly prepared enzymes (Urokinase mixed with enzymes including but not limiting to collagenase enzymes (either Type I or Type II) and Hyaluronidase, and in presence or absence of HSP 70 (protein) suspended in Hank's balanced salt solution (1X-HBSS)) and incubated for 20-30 min at 37° C. in a shaking incubator at 150 rpm. Further, 10 ml of growth medium in the clotted biopsy-enzyme solution was added and vigorously mixed to form a suspension using 25 ml sterile pipette. The above vigorous mixing procedure was repeated for 3-4 times. Growth medium containing bone marrow sample was filtered with 50-100 μM cell strainer followed by centrifugation at 1300-1800 rpm for 10-15 min. After centrifugation, the supernatant was discarded, and cell pellet was dissolved with growth medium (DMEM with 10% PL/FBS). Different tests viz., cell count, cell viability (refer Table 1) and other QC tests viz., sterility and *Mycoplasma* were performed. 1 ml each of the nucleated cells of bone marrow cell suspension were seeded in four 35 mm Petri plates/culture flasks for confirmation of CFU test and cell characterization was conducted through flow cytometry. Remaining cell suspension was seeded in T75 tissue culture grade cell culture flasks for further culture, differentiation into osteoblasts and their expansion with different combination of medium viz., DMEM, F12, RPMI and α-MEM along with 10% umbilical cord blood (UCB) and maternal blood (MB) derived Platelet lysate (PL) or with FBS, along with growth factor, FGF. Table 1 shows a comparative data of isolating bone marrow nucleated cells from clotted bone marrow in presence of: (a) urokinase (UK)+ hyaluronidase (HA)+ collagenase Type-I (Col-I); and (b) UK+HA+Col-I+heat shock protein 70 (HSP70).

TABLE 1

| | Isolation of bone marrow nucleated cells from Clotted bone marrow | | | |
|---|---|---|---|---|
| | UK + HA + Col-I | | UK + HA + Col-I + HSP70 | |
| Sample ID | Cell count at isolation stage | Cell viability at isolation stage (%) | Cell count at isolation stage | Cell viability at isolation stage (%) |
| Sample-01 | $5.1 \times 10^6$ | 98.2 | $7.1 \times 10^6$ | 98.6 |
| Sample-02 | $4.4 \times 10^6$ | 97.5 | $6.7 \times 10^6$ | 97.8 |
| Sample-03 | $3.6 \times 10^6$ | 96.4 | $6.6 \times 10^6$ | 97.1 |
| Sample-04 | $4.8 \times 10^6$ | 95.7 | $5.9 \times 10^6$ | 95.4 |
| Sample-05 | $5.6 \times 10^6$ | 90.8 | $6.4 \times 10^6$ | 92.2 |

One in the art would appreciate from the data above (Table 1), the efficacious isolation of MSCs from clotted bone marrow using the procedure of the present disclosure. Further, to enhance the cell yield from clotted bone marrow, when Heat Shock protein 70 (HSP 70) was mixed with urokinase, collagenase and hyaluronidase in concentration of 100 ng/ml-1 μg ml, the bone marrow clot dissolved completely, and cell recovery was greater.

Within the two methods having different combination of enzymes, it can be observed that the combination comprising UK+HA+Col-I+HSP70 provided higher cell count in all the five samples, and the change with respect to the cell viability is almost minimal.

Example 4

Initial Characterization of Osteoprogenitor/MSCS by Using Flow Cytometry and MSC-CFU Assay:

Cells that were seeded for MSC-CFU assay and flow cytometry for initial cell characterization in four 90 mm cell culture Petri plates, were used. Bone marrow samples (2 ml each) were seeded in 90 mm Petri plate cultured with α-MEM and 10% UCB+MB PL or FBS, 2 mM L-Glutamine and 1× pen-strep antibiotics (growth medium) along with growth factors, such as 1-10 ng/ml FGF. These Petri plates were further incubated in $CO_2$ incubator with 5% $CO_2$ at 37° C.

Medium changes (α-MEM and 10% UCB+MB PL or FBS) were given at subsequence intervals of 2-4 days up to 12-14 days in order to replenish the media which got depleted during cell growth and multiplication; which otherwise would have caused depletion of media or provided acidic nature to the culture media leading to improper growth. Therefore, media was changed at regular intervals.

MSC-CFU Assay:

Identification of MSCs Using CFU-F Assay

CFU-F assay was used to enumerate or identify the number of MSCs within a given heterogeneous population of cells isolated from bone marrow. It was carried out by using freshly isolated primary cells from bone marrow.

Use of Crystal Violet Staining for CFU-F Assay:

Preparation of Early Passage MSCs for the CFU-F Assay:

Harvested bone marrow derived primary cells were seeded in 90 mm Petri plate with growth medium as described above. Medium changes were given at alternate day. Cells were incubated in $CO_2$ incubator at 37° C. at 5% $CO_2$ under humidified conditions. On day 14±3, cultured cells were taken out from incubator and observed under microscope for growth of the cells. After confirmation of growth, the cells were analyzed for crystal violet staining.

Procedure for Staining the CFU-F:

After 14±3 days of culture, petri plates were removed from the $CO_2$ incubator, cell culture medium was pipetted out and cells were washed with buffer for three times. Cells were stained with 0.5% of crystal violet solution freshly prepared in methanol and incubated at room temperature for 30 minutes. Stain was discarded and then plate washed with buffer followed by air drying.

Counting Colonies:

Stained cells were observed under inverted microscope. Inverted 90 mm dish and score bottom of dish into four equal quadrants. 90 mm dish was placed, inverted onto the stage of a dissection microscope. Colonies were enumerated of each plate. By definition, a colony was having a minimum of 50 cells to be enumerated. After counting the colonies photographs of the same were taken under 100× magnification.

Results: MSC CFU-F Assay:

Table 2 below demonstrates the results of Crystal violet staining observed in the stained plate containing BM-MSCs colonies at 14±3 days of culture.

TABLE 2

Number of colonies obtained with Crystal violet staining:

| Sr. No | Sample ID | Result | Remark | No. of colonies obtained |
|---|---|---|---|---|
| 1 | Sample BM-MSC 01 | Positive | Stained MSC in colonies were observed | 25 |
| 2 | Sample BM-MSC 02 | Positive | Stained MSC in colonies were observed | 35 |
| 3 | Sample BM-MSC 03 | Positive | Stained MSC in colonies were observed | 45 |
| 4 | Sample BM-MSC 04 | Positive | Stained MSC in colonies were observed | 27 |
| 5 | Sample BM-MSC 05 | Positive | Stained MSC in colonies were observed | 24 |

Figure 4:
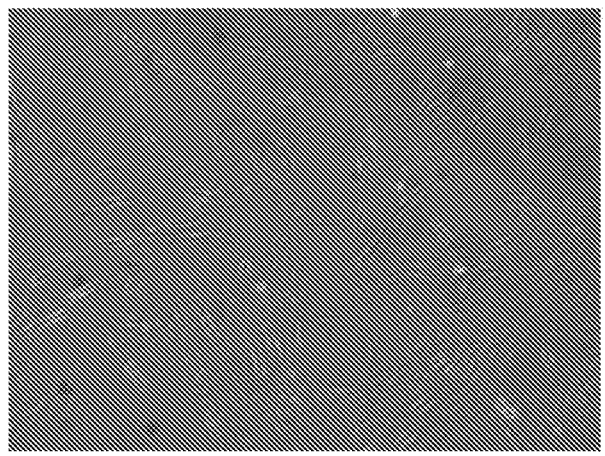
FIG. 4 illustrates Bone Marrow Mesenchymal Cells (BM-MSCs) before staining at 100× magnification, in accordance with an embodiment of the present disclosure.
Figure 5:
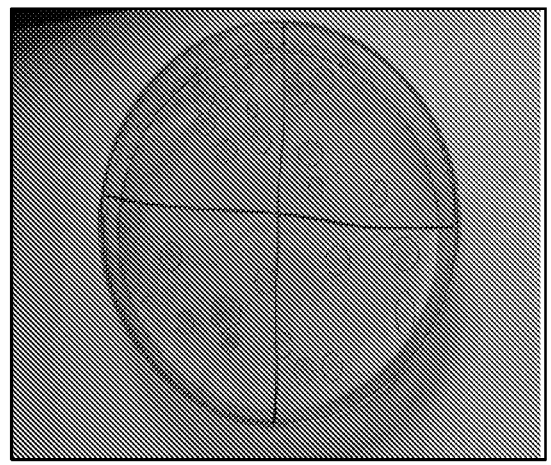
FIG. 5 illustrates Crystal violet staining showing stained BM-MSC colonies in Petri plates, in accordance with an embodiment of the present disclosure.
Figure 6I:
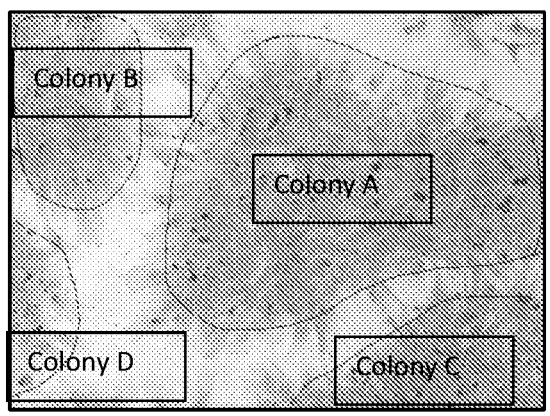
FIG. 6 illustrates in part (i) and (ii) the BM-MSC-derived CFU-F colonies from clotted bone marrow sample at 100× magnification after Crystal violet staining, in accordance with an embodiment of the present disclosure.
Figure 6I:
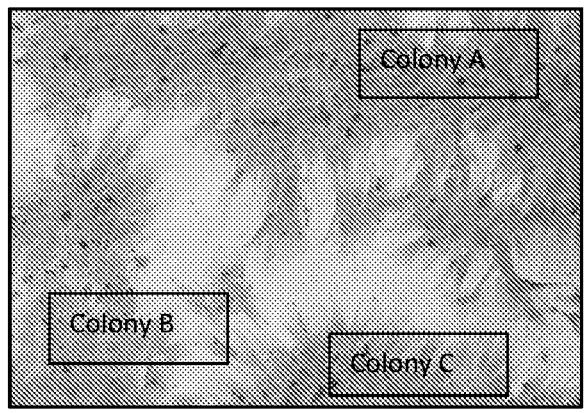

Histochemical Characterization:

FIG. 4 demonstrates bone marrow mesenchymal cells (BM-MSCs) before staining at 100× magnification. FIG. 5 illustrates Crystal violet staining showing stained BM-MSC colonies in Petri plates. Further, FIGS. 6(i) and 6(ii) show BM-MSC-derived CFU-F colonies from clotted bone marrow sample at 100× magnification after Crystal violet staining.

Characterization of BM-MSCs Using Flow Cytometry:

Around 1 million of cultured cell suspension was taken for cell characterization through flow cytometry. They were tested for cell surface markers including, CD90, CD73, and CD105 as positive cell-surface and lineage markers and CD34 and HLA-DR as negative markers for cell lineage based on their expression.

Marker Characterization:

Cultured BMSCs (after 14±3 days) were harvested by the process of trypsinization. Immunophenotypic characterization was performed by Fluorescence-Activated Cell Sorter (FACS) on a BD (Becton, Dickinson) FACS CANTO-2. Fluorescence excitation was carried out by using an argon-ion and a red LASER of 488 nm and 632 nm, respectively. The fluorescence emission was collected by using corresponding detectors. Approximately $1 \times 10^6$ cells were stained with predefined antibody cocktails I i.e. (CD90, CD73, CD105, HLA-DR and CD34). The stained cells were incubated in the dark for 20 min at room temperature, washed with FACS flow buffer (BD Biosciences) and resuspended in FACS flow buffer and then analyzed on a BD FACS canto-2. Data acquisition and analysis were accomplished by using BD FACS Diva software (BD Biosciences) (Table 3).

TABLE 3

Cell surface marker expression for BM - MSCs after 14 ± 3 days of culture using Flow cytometry:

| | | Cell Surface Expression (%) | | | | |
|---|---|---|---|---|---|---|
| Sr. No. | Sample ID | CD73 | CD90 | CD105 | HLA-DR | CD34 |
| 1 | Sample BM-MSC 01 | 99.8 | 99.9 | 100 | 0.1 | 3.6 |
| 2 | Sample BM-MSC 02 | 100 | 99.9 | 100 | 0.1 | 3.5 |
| 3 | Sample BM-MSC 03 | 99.9 | 100 | 100 | 0.0 | 4.8 |
| 4 | Sample BM-MSC 04 | 99.8 | 100 | 100 | 0.2 | 3.2 |
| 5 | Sample BM-MSC 05 | 94.2 | 94.9 | 92.3 | 1.0 | 1.8 |

FIG. 7 demonstrates representative FACS data that shows immunophenotypic results using flow cytometry for bone marrow derived MSCs at 14±3 days of culture showing CD90 and CD105 positive expression and CD34 negative expression.

FIG. 8 demonstrates representative FACS data that shows immunophenotypic results using flow cytometry for bone marrow derived MSCs at 14±3 days of culture showing CD73 positive expression and HLA DR negative expression.

Example 5

Differentiation of Bone Marrow Derived MSCs into Osteoblast Cells:

After 2-5 days of seeding of bone marrow nucleated cells, non-adhered cells were washed out during the process of medium change. To the adhered cells, bone differentiation medium with combinations of 60% α-MEM, 30% IMDM and L-glutamine (2 mM) with 10% UCB+MB PL or FBS was added. Differentiation factors such as, dexamethasone, β-glycerophosphate and L-ascorbic acid were subsequently added to the medium. Growth factors such as, FGF, TGF, IGF were also added to the differentiated medium. 10 ml each of freshly prepared medium were added to the culture flasks and flasks were further incubated in $CO_2$ incubator under humidified conditions (>80% humidity) with 5% $CO_2$ at 37° C. to reach the differentiating cells ready for sub-culture called the passage ready cells (P0 or $P_0$ cells).

Example 6

Expansion and Comparison with UCB+MB PL or FBS:
Expansion:

After initiation of differentiation of MSCs into osteoblasts, media changes (EMEM+F12+FBS/PL) were given at subsequence intervals (every three days) to achieve >70% confluency at first passage stage (P1 or P(1) or $P_1$ cells, viz., the pre-osteoblast cells) which took around 12-15 days. Cell were washed thrice with the 1×DPBS followed by treating with 0.25% trypsin and incubated the cells at 370C for 5 mins, followed by neutralizing the incubated cells with the complete media (EMEM+F12+FBS/PL). Cells were collected in growth media (EMEM+F12+FBS/PL) and centrifuged at 1300-1800 rpm for 5-10 mins. Cell count, cell viability (see Table 4), sterility and *Mycoplasma* (see Table 5) were done subsequently. Cell characterization with the help of flow cytometry and RT-PCR studies were also performed. For the cell characterization by flow cytometry alkaline phosphatase (ALP) as a positive marker and for RT-PCR, ALP, collagen-1, osterix and Runx were tested as differentiation markers and rest of the cells are cryopreserved.

Culturing of Bone Cells Using FBS and Umbilical Cord Blood Derived Platelet Lysate (PL) with Maternal Blood Platelet Lysate:

In this study, the effect of UCB+MB PL on cell growth when added to medium and the same were compared with cell culture medium supplemented with FBS. Total cell suspension was divided into two parts and these two parts were cultured separately. One part contained a combination of DMEM, F12, RPMI and α-MEM with 10% UCB+MB PL and another part contained cell suspension cultured in combination of DMEM, F12, RPMI and α-MEM with 10% FBS. In both the cases, cells were seeded with seeding density of 3000 to 5000 cells/cm² in T-150 cell culture flasks. Medium changes were given at subsequent intervals of 2-4 days to achieve >70% at second passage stage (P2 or P(2) or $P_2$ cells, viz., the transplantation-ready osteoblast cells) for around 12-15 days. Cell were washed with the 1×DPBS followed by treating the rewashed cells with 0.25% trypsin and incubated the cells at 37° C. for 5 mins followed by neutralizing the incubated cells with the complete media. Cells were collected with growth media and centrifuged at 1300-1800 rpm for 5-10 mins (Refer to Table 4 and Table 5 for the cell analysis data)

TABLE 4

Cell analysis at Passage 1 stage and Comparison of (UCB + MB) PL and FBS use in cell culture medium to check growth, viability and cell surface expression:

| Sample ID | Cell count at P(1) stage- PL | Cell count at P(1) stage- FBS | Cell viability (%) at P(1) stage- PL | Cell viability (%) at P(1) stage- FBS | ALP marker expression (%)- PL | ALP marker expression (%)- FBS | Sterility | Mycoplasma |
|---|---|---|---|---|---|---|---|---|
| Sample-01 | 14.28 | 14.34 | 97.95 | 98.52 | 90 | 94.9 | No growth | Negative |
| Sample-02 | 17.79 | 16.45 | 96.15 | 98.02 | 96 | 96.4 | No growth | Negative |
| Sample-03 | 17.73 | 13.08 | 95.97 | 96.55 | 92.2 | 87.3 | No growth | Negative |
| Sample-04 | 19.71 | 15.69 | 96.73 | 97.98 | 91 | 99.1 | No growth | Negative |
| Sample-05 | 16.23 | 12.28 | 96.09 | 95.89 | 90.5 | 93 | No growth | Negative |
| Sample-06 | 17.5 | 12.66 | 97.36 | 97.7 | 97.6 | 96.6 | No growth | Negative |
| Sample-07 | 17.76 | 19.18 | 98.59 | 98.3 | 90.1 | 93.1 | No growth | Negative |
| Sample-08 | 18.9 | 16.16 | 97.4 | 97.79 | 95.1 | 97.4 | No growth | Negative |
| Sample-09 | 18.83 | 8.6 | 96.73 | 96.56 | 94.4 | 96.8 | No growth | Negative |
| Sample-10 | 15.21 | 15.3 | 95.28 | 97.89 | 93.7 | 97.9 | No growth | Negative |
| Sample-11 | 17.36 | 21.06 | 96.2 | 98.61 | 92 | 93.9 | No growth | Negative |
| Sample-12 | 16.43 | 5.71 | 94.04 | 96.59 | 90.9 | 89.2 | No growth | Negative |

TABLE 4-continued

Cell analysis at Passage 1 stage and Comparison of (UCB + MB) PL and FBS
use in cell culture medium to check growth, viability and cell surface expression:

| Sample ID | Cell count at P(1) stage- PL | Cell count at P(1) stage- FBS | Cell viability (%) at P(1) stage- PL | Cell viability (%) at P(1) stage- FBS | ALP marker expression (%)- PL | ALP marker expression (%)- FBS | Sterility | Mycoplasma |
|---|---|---|---|---|---|---|---|---|
| Sample-13 | 15.6 | 15.78 | 93.87 | 98.06 | 92.8 | 81.1 | No growth | Negative |
| Sample-14 | 15.7 | 16.03 | 95.08 | 97.42 | 90.4 | 94.1 | No growth | Negative |
| Sample-15 | 14.39 | 17.68 | 96.65 | 98.52 | 93.4 | 91.6 | No growth | Negative |

TABLE 5

Cell analysis at Manufacturing (Passage 2) stage and Comparison of (UCB + MB) PL
and FBS use in cell culture medium to check growth, viability and cell surface expression

| Sample ID | Cell count ($10^6$) at MFG stage- PL | Cell count ($10^6$) at MFG stage- FBS | Cell viability (%) at MFG stage- PL | Cell viability (%) at MFG stage- FBS | Endotoxin at MFG stage- PL (EU/ml) | Endotoxin at MFG stage- FBS (EU/ml) | Cell purity at MFG stage- PL (g/dL) | Cell purity at MFG stage- FBS (g/dL) | ALP marker expression (%)- PL at MFG | ALP marker expression (%)- FBS at MFG |
|---|---|---|---|---|---|---|---|---|---|---|
| MFG-01 | 58.54 | 56.64 | 97.45 | 96.43 | <0.750 | <0.850 | 0.140 | 0.150 | 96.9 | 95.8 |
| MFG-02 | 60.21 | 58.34 | 97.23 | 97.32 | <0.600 | <0.650 | 0.168 | 0.173 | 97.5 | 96.6 |
| MFG-03 | 57.35 | 57.80 | 98.22 | 98.35 | <0.900 | <0.900 | 0.164 | 0.175 | 97.6 | 91.3 |
| MFG-04 | 53.46 | 51.46 | 97.69 | 96.88 | <0.800 | <0.850 | 0.209 | 0.212 | 98.1 | 95.9 |
| MFG-05 | 59.56 | 58.33 | 97.33 | 95.49 | <0.800 | <0.800 | 0.190 | 0.192 | 97.3 | 94.3 |

Sterility and *Mycoplasma* were tested negative for all the samples. Further, no chromosomal aberrations were observed during Karyotyping for all the samples.

Example 7

Cryopreservation:

P1 stage cells were cryopreserved at approximately 10-20 million cells, which were pre-osteoblastic stage cells. These cells were then reprocessed using sub-culturing medium to P2 stage mature osteoblast cells, where not less than 48 million cells were achieved; which were then transplanted to the targeted site.

Rest of the cells at P1 stage cells were cryopreserved for 6, 12 and 24-months using cell freezing medium containing 90% of FBS+10% DMSO. Based on the cell count, at least $5 \times 10^6$ cells are cryopreserved in minimum of 3 cryovials. Further these cryovials were subjected to process of controlled freezing using Control rate freezer and reduced temperature up to −50° C. with 10° C. per min freezing rate with the help of liquid nitrogen and after attaining temperature at −50° C., the cryovials were immediately transferred at a temperature below −150° C. in liquid nitrogen tank (under Vapor phase conditions).

Example 8

Reprocess of Cryopreserved Samples:

Cryopreserved cells were thawed and reprocessed at different time intervals such as 6, 12 and 24 months. In this process, cryopreserved vials were removed from liquid nitrogen tank and immediately thawed, by transferring the vials containing the cells into water bath at 37° C. After thawing, the cell suspension from cryovial was transferred to growth medium (α-MEM, F12 with FGF) containing 10% of UCB+MB PL or FBS and centrifuged at 1200-1800 rpm for 5-10 mins. Supernatant was discarded, and the cell pellet was further suspended in culture medium ((α-MEM, F12 with FGF) containing 10% of UCB+MB PL) and cell count and cell viability tests are performed, and their observations are recorded (refer Tables 6, 7, and 8).

TABLE 6

Bone cell 6-months cryopreservation results:

| Sample ID | Cell count at reprocess P(1) stage | Cell viability | Cell count at P(2) stage | Cell viability | Cell characterization- ALP marker expression (%) |
|---|---|---|---|---|---|
| Sample-01 | 5.2 | 96.65% | 48.84 | 98.74% | 93.5 |
| Sample-02 | 6.4 | 95.45% | 56.04 | 96.95% | 95.78 |
| Sample-03 | 6.73 | 93.97% | 64.85 | 95.89% | 92.22 |
| Sample-04 | 7.71 | 96.73% | 66.19 | 97.33% | 90.8 |
| Sample-05 | 5.23 | 93.29% | 49.6 | 97.33% | 90.5 |

Number of days required for culture of cells from P1 reprocess to P2 stage was 15 days ± 3 days

TABLE 7

Bone cell 12-months cryopreservation results:

| Sample ID | Cell count at Reprocess P(1) stage | Cell viability at Reprocess P(1) stage | Cell count at P(2) stage | Cell viability at P(2) stage | Cell characterization- ALP marker expression (%) |
|---|---|---|---|---|---|
| Sample-06 | 7.5 | 94.67% | 59.5 | 97.42% | 96.3 |
| Sample-07 | 6.76 | 93.41% | 54.15 | 98.52% | 92.1 |
| Sample-08 | 5.8 | 95.40% | 53.92 | 96.37% | 96.7 |
| Sample-09 | 7.83 | 92.37% | 61.72 | 96.41% | 97.4 |
| Sample-10 | 5.21 | 94.88% | 49.57 | 98.68% | 95.7 |

Number of days required for culture of cells from P1 reprocess to P2 stage was 15 days ± 3 days

TABLE 8

Bone cell 24-months cryopreservation results:

| Sample ID | Cell count at reprocess P(1) stage | Cell viability at Reprocess P(1) stage | Cell count at P(2) stage | Cell viability | Cell characterization- ALP marker expression (%) |
|---|---|---|---|---|---|
| Sample-11 | 6.88 | 90.20% | 58.55 | 94.22% | 95.1 |
| Sample-12 | 5.75 | 89.44% | 48.93 | 93.47% | 93.9 |
| Sample-13 | 6.78 | 91.24% | 59.72 | 96.11% | 98.8 |
| Sample-14 | 7.7 | 91.28% | 64.52 | 95.63% | 94.3 |
| Sample-15 | 6.25 | 92.75% | 48.48 | 96.58% | 96.4 |

Number of days required for culture of cells from P1 reprocess to P2 stage was 15 days ± 3 days

Example 9

MFG (Manufacturing) OC:

At Passage 2 (P2), cells were harvested from cell culture flasks and observed that in all samples over 48 million cells, with a cell viability of over 90% was achieved (refer Table 5). Quality control (QC) tests such as sterility, *Mycoplasma*, cell purity, endotoxin, Alizarin red staining (see FIGS. 9 and 10) and karyotyping analysis (chromosomal abnormalities) at initial level and the final product were performed (see FIG. 11) and found as per specifications. Cell characterization was performed with the help of flow cytometry. For the cell characterization by flow cytometry alkaline phosphatase (ALP+) surface marker was tested.

In RT-PCR studies (refer to Table 12), different genes involved in bone remodeling as well as negative expression were checked. Genes, viz, ALP, collagen-1, Osterix, Ephrin B4 and Runx markers were tested for and to confirm osteoblast cells. MEPE marker for osteocyte cells, ICAM and leptin receptor markers for bone lining cells and Ephrin B2 marker for osteoclast cells were also tested in osteoblasts. Similarly, MSCs gene expression studies were also performed on cultured osteoblasts cells to check if any MSCs population is mixed with osteoblast cells.

Typical analysis of the osteoprogenitors/osteoblasts involves Appearance, Sterility, *Mycoplasma*, Endotoxin, Cell Counting, Cell Viability, Cell Purity Test, Cell Characterization and Karyotyping Analysis. Karyotyping analysis of final product of cultured osteoblast cells showed no cell transformation. Thus, the isolated MSCs which were cultured to adult live and mature osteoblasts maintained normal karyotype in long-term cultures (Refer to Table 9 for the results of Alizarin Red S staining).

TABLE 9

Alizarin Red S staining in Osteoblasts cultured at 28 days ± 3 days:

| Sr. No | Sample ID | Result | Observation |
|---|---|---|---|
| 1 | MFG-01 | Positive | Stained calcified nodules observed |
| 2 | MFG-02 | Positive | Stained calcified nodules observed |
| 3 | MFG-03 | Positive | Stained calcified nodules observed |
| 4 | MFG-04 | Positive | Stained calcified nodules observed |
| 5 | MFG-05 | Positive | Stained calcified nodules observed |

FIG. 9 and FIG. 10 show representative images of stained calcified nodules, i.e., final product of cultured osteoblast cells in the culture using Alizarin red mineralization stain, which were taken under 100× and 40× magnification, respectively of inverted microscope.

Example 10

Gene Expression:
RT-PCR Expressions:

Total RNA was isolated from the cultured BM-MSCs and the differentiated osteoblasts cells by total RNA extraction method. Extracted RNA was quantified and using reverse transcriptase technique, RNA was transcribed in the presence of oligo-dT primers for complementary DNA (cDNA) synthesis. The expression of different genes was assessed by using SYBR-Green RT-PCR master mix. Real-time PCR Master Mix containing, Syber green probes, specific primers, and cDNA were mixed, and real-time RT-PCR was performed using a Rotar gene Q Real-Time RT-PCR. The primers used are shown in the below Table 10. Gene expressions was normalized to the reference gene GAPDH and calculated as the relative as the relative expression compared to control cells. Comparative analysis of the 12 different gene expression was done in cultured MSCs, differentiated pre-osteoblasts and mature osteoblasts with fold of gene expressions.

TABLE 10

Primer sequences:

| Name of the Genes | species | Forward Primer sequence* (5'→3') | Reverse (5'→3') |
|---|---|---|---|
| OCT-4 | Human | GTTGATCCTCGGACCTGGCTA (SEQ ID NO: 1) | GGTTGCCTCTCA CTCGGTTCT (SEQ ID NO: 2) |
| Nanog | Human | GTCTTCTGCTGAGATGCCTCACA (SEQ ID NO: 3) | CTTCTGCGTCAC ACCATTGCTAT (SEQ ID NO: 4) |

TABLE 10-continued

Primer sequences:

| Name of the Genes | species | Primer sequence* Forward (5'→3') | Reverse (5'→3') |
|---|---|---|---|
| Sox2 | Human | GCCGAGTGGAAACTTTTGTCG (SEQ ID NO: 5) | GCAGCGTGTACT TATCCTTCTT (SEQ ID NO: 6) |
| ALP | Human | ACCATTCCCACGTCTTCACATTT (SEQ ID NO: 7) | AGACATTCTCTC GTTCAC CGCC (SEQ ID NO: 8) |
| Collagen-1 | Human | GGACACAATGGATTGCAAGGCCC (SEQ ID NO: 9) | TAACCACTGCTC CACTCTGGATGG (SEQ ID NO: 10) |
| RunX2 | Human | AGATGATGACACTGCCACCTCTG (SEQ ID NO: 11) | GGGATGAAATGC TTGGGAACT (SEQ ID NO: 12) |
| Osterix | Human | TAGTGGTTTGGGGTTTGTTTTACCGC (SEQ ID NO: 13) | AACCAACTCACTCTTATTCCCTAAGT (SEQ ID NO: 14) |
| ICAM-1 | Human | GGCCGGCCAGCTTATACAC (SEQ ID NO: 15) | TAGACACTTGAG CTCGGGCA (SEQ ID NO: 16) |
| Leptin receptor | Human | AGGAAGCCCGAAGTTGTGTT (SEQ ID NO: 17) | TCTGGTCCCGTC AATCTGA (SEQ ID NO: 18) |
| Ephrin B2 | Human | GCATCTGTCTGCTTGGTCTTTATCAAC (SEQ ID NO: 19) | ATGGCTGTGAGA AGGGACTCC (SEQ ID NO: 20) |
| Ephrin B4 | Human | GAAGAAGGAGAGCTGTGTGGCAATC (SEQ ID NO: 21) | GATGACTGTGAA CTGTCCGTCGTT (SEQ ID NO: 22) |
| MEPE | Human | CGAGTTTTCTGTGTGGGACTACTC (SEQ ID NO: 23) | CTTAGTTTTCTCA GTCTGTGGTTGAAAT (SEQ ID NO: 24) |

*Oligonucleotide sequences of sense (S) and antisense (A) primers used in the real-time PCR of target and housekeeping gene.

TABLE 11

List of RT-PCR markers used at Passage 1 (P1) and Passage 2 (P2) stages:

| Markers | MSC | Pre-osteoblast | Osteo-blast | Osteo-cyte | Bone lining cells (BLC) | Osteo-clast |
|---|---|---|---|---|---|---|
| OCT-4 | +++ | − | − | − | − | − |
| Nanog | +++ | − | − | − | − | − |
| Sox2 | +++ | − | − | − | − | − |
| ALP | − | + | +++ | − | | |
| Collagen-1 | − | ++ | +++ | − | | |
| RunX2 | | ++ | +++ | − | | |
| Ephrin B4 | − | − | +++ | − | − | |
| Osterix | − | ++ | +++ | − | − | |
| MEPE | − | − | − | + | − | − |
| ICAM-1 | + | − | − | − | + | − |
| Leptin receptor | + | − | − | − | + | − |
| Ephrin B2 | − | − | − | −− | | + |

TABLE 12

Results of gene expression evaluated by RT-PCR analysis:

| Genes | Sample-01-Fold of expression | | | Sample-02- Fold of expression | | | Sample-03- Fold of expression | | | Sample 04 - Fold of expression Mature |
|---|---|---|---|---|---|---|---|---|---|---|
| | MSC ($P_0$) | Pre-osteoblast ($P_1$) | Mature osteoblast ($P_2$) | MSC ($P_0$) | Pre-osteoblast ($P_1$) | Mature osteoblast ($P_2$) | MSC ($P_0$) | Pre-osteoblast ($P_1$) | Mature osteoblast ($P_2$) | Osteoblasts after 24 months of cryopreservation |
| Oct-4 | 1 | 0.49 | 0.45 | 1 | 0.16 | 0.4 | 1 | 1.4 | 1.31 | 1.29 |
| Nanog | 1 | 1.15 | 0.98 | 1 | 1.18 | 0.74 | 1 | 1.18 | 1.31 | 1.32 |
| sox2 | 1 | 1.18 | 0.8 | 1 | 1.26 | 1.45 | 1 | 1.49 | 0.89 | 0.78 |
| ALP | 1 | 4 | 9 | 1 | 1 | 2 | 1 | 4.8 | 6.7 | 6.9 |
| Collagen-1 | 1 | 8 | 11 | 1 | 1 | 2 | 1 | 5.2 | 8.7 | 8.6 |
| runx2 | 1 | 4 | 9.5 | 1 | 2 | 4 | 1 | 4.7 | 5.9 | 5.7 |
| OSTERIX | 1 | 8 | 13.5 | 1 | 2 | 4 | 1 | 3.7 | 4.5 | 4.3 |
| ICAM -I | 1 | 0 | 0 | 1 | 0 | 0 | 1 | 0.2 | 1 | 1 |
| leptin | 1 | 2 | 1.4 | 1 | 0.5 | 1 | 1 | 2.2 | 0.1 | 0.1 |
| ephrinB4 | 1 | 1.8 | 2.8 | 1 | 3.2 | 4.6 | 1 | 7.5 | 10.6 | 10.3 |
| MEPE | 1 | 2 | 2 | 1 | 2 | 2 | 1 | 6.8 | 5.9 | 5.8 |
| Ephrin-b2 | 1 | 0.4 | 0.3 | 1 | 0 | 0.3 | 1 | 0.3 | 0.8 | 0.7 |

Conclusion from the RT-PCR Experiments (Summarized in Table 12):

Oct4 Expression: At P0 stage shows higher expression compare to P1 (pre-osteoblast) and P2 (mature osteoblast) stage.

Nanog Expression: At P0 shows expression and P1 stage little more expression than P0 but at P2 stage it showed lower than P0 stage.

SOX2 Expression: At P0 shows expression and P1 stage little more expression than P0 but at P2 stage it showed lower than P0 stage.

ALP Expression: Compare to P0 stage, P1 and P2 stages showed higher expression.

Collagen-1 expression: Compare to P0 stage, P1 and P2 stages showed higher expression.

RunX2 expression: Compare to P0 stage, P1 and P2 stages showed higher expression.

Osterix Expression: Compare to P0 stage, P1 and P2 stages showed higher expression ICAM1 expression: At P0 stage showed expression and very less expression at P1 and P2 stages.

Leptin expression: At P0 showed expression and P1 stage little more expression than P0 but at P2 stage it showed lower than P0 stage.

Ephrin B4 expression: Compare to P0 stage, P1 and P2 stages showed higher expression.

MEPE Expression: Compare to P0 stage, P1 and P2 stages showed higher expression.

Ephrin b2 expression: At P0 stage showed expression and very less expression at P1 and P2 stages.

The temporal expression of Oct-4, Nanog, SOX2, ALP, Collagen-1, RUNX2, OSTERIX, ICAM-I, Leptin, Ephrin B4, MEPE and Ephrin-b2 was studied to evaluate osteoblastic phenotypic properties. The gene expression results were similar with what has been seen in in-vivo bone remodeling systems. In general, the expression levels of collagen type-I, RUNX2, OSTERIX and ALP were upregulated in the cell cultures in the differentiated and expansion medium of the invention. The expressions of alkaline phosphatase (ALP), RUNX2 and Osterix genes on the culture plates showed increasing levels with increasing culturing phase/time. The stage-wise increase in the expression of RUNX2, Osterix, and ALP is the key to detecting osteoblasts during culturing. It can be observed that even after cryopreservation till 24 months the gene expression is on a higher end, thereby, confirming the integrity of the osteoblasts even upon cryopreservation. Further, gene expression folds of less than one was observed in case of Ephrin-b2 for mature osteoblast cells. Since Ephrin-b2 is an indicator of osteoclasts, therefore, it can be inferred that the mature osteoblasts are not differentiating into intracell lineages. The expression of Oct-4, Nanog, SOX2 seen in cultured MSCs were further downregulated in the differentiated osteoblasts cultures of the optimized medium. The expression of ICAM-I and Leptin were also downregulated. ICAM-I and Leptin markers of Bone lining cells are known to be predominantly expressed in the fully formed bone cells in in-vivo bone union. Thus, a person of skill in the art would understand that this downregulation of these gene expression is a confirmatory result of obtaining adult, live, mature osteoblasts in the culture medium.

Example 11

In Process Quality Control (IPQC) Details:

TABLE 13

| Quality control result summary: | | |
|---|---|---|
| Processing Stage | Test (As applicable) | Acceptance Criteria |
| Isolation | Mycoplasma | Negative |
| | Sterility | Negative/No growth |
| | Cell Count | ≥5,000,000 cells |
| | Cell Viability | ≥80% dye excluding cells |
| P1 Subculture | Mycoplasma | Negative |
| | Sterility | Negative/No growth |
| | Karyotypic Analysis | No chromosomal Abnormalities |
| | Cell Count | ≥5,000,000 cells |
| | Cell Viability | ≥80% dye excluding cells |
| P2 Sampling | Sterility (72 hours before Manufacturing) | Negative/No growth |
| Manufacturing | Cell Count | Over 12,000,000 cells/vial |
| | Cell Viability | ≥80% Dye Excluding Cells |
| | Cell Purity Test | <1 g/dL |
| | Cell Characterization | ≥80% BONE ALP$^+$ CELLS |
| | Histochemical test | Stained calcified nodules |
| | Mycoplasma | Negative |
| | Endotoxin test | <3 EU/ml |
| | Karyotypic Analysis | No chromosomal Abnormalities |

Example 12

Release Product Specification:

Specification of the final product which is an autologous product for medical use are provided in the Table 14 herein below. To check the quality of the product we have design the specification of the product.

TABLE 14

Final product based on mixing of umbilical cord blood and maternal blood platelet rich plasma to obtain umbilical cord blood and maternal blood platelet rich plasma platelet lysate (UCB + MB PL):

| | Parameter/tests | Acceptable limit Final product |
|---|---|---|
| 1.1 | Cell number | NLT 48,000,000 cells |
| 1.2 | Cell viability | ≥80% dye - excluding cells |
| 1.3 | Microbial sterility | Negative |
| 1.4 | Endotoxin | <3 EU/ml |
| 1.5 | Mycoplasma | Negative |
| 1.6 | Cell purity test | <1 g/dl |
| 1.7 | Cell characterization | ≥80% bone ALP$^+$ cells |
| 1.8 | Histochemical test- Alizarin red staining | Stained calcified nodules |
| 1.9 | Karyotypic analysis | No chromosomal abnormalities |

NLT: not less than

ADVANTAGES OF THE PRESENT DISCLOSURE

The present disclosure discloses a method for obtaining pure, adult, live, mature osteoblastic or osteoprogenitor cells from clotted bone marrow samples, which has traditionally been a difficult task. The present disclosure provides a unique set of enzyme combinations and mechanical treatments against the clotted sample to procure maximal cells. The present disclosure also provides different media combinations along with growth factors, and a unique platelet lysate derived from a combination of discarded umbilical cord blood and maternal blood platelet-rich plasma (instead of animal origin serum) and standardizing it to an optimal ratio of different media combinations for an optimized osteoprogenitor differentiation into osteoblasts and their expansion hereafter. The present disclosure provides preparation and standardization of method including the use of unique enzymes demonstrating capacity for isolation of osteoprogenitor/MSCs from clotted bone marrow. Further, the present disclosure identifies several genes involved in the bone remodeling process of osteogenesis expressed through the cell culture of the starting material (clotted bone marrow) until the preparation of final product (characterized transplantation-ready osteoblast cells). The present disclosure also teaches method of creating of patient-specific cell dose, adult live osteoblast not less than 48 million cells from each batch of clotted bone marrow sample/biopsy for cell therapy application of bone diseases in human. The assessment of RT-PCR results captures the in-vivo bone remodeling process under in-vitro conditions to reach the transplantation-ready osteoblasts which are likely to assimilate better post-transplantation. Also, the method of preparation taught by the present disclosure is usable for wide scope of sample and not limited to clotted marrow samples and achieving 48 million cell dosage.

---

We claim:

1. A method for preparing a mesenchymal stem cell suspension from a clotted bone marrow, said method comprising:
   a) obtaining a bone marrow sample, wherein the bone marrow sample comprises clotted bone marrow;
   b) chopping the clotted bone marrow into pieces of at least 2 mm$^3$ to obtain chopped clotted bone marrow;
   c) contacting the chopped clotted bone marrow with at least one enzyme and at least one protein in the presence of a buffer to obtain a clotted bone marrow reaction solution, wherein the at least one protein is selected from the group consisting of heat shock proteins and combinations thereof;
   d) incubating the clotted bone marrow reaction solution at a temperature of at least 35° C. for a time of at least 20 minutes to obtain an incubated clotted bone marrow reaction solution;
   e) contacting the incubated clotted bone marrow reaction solution of step (d) with a growth medium to obtain a suspension;
   f) mixing the suspension for a plurality of repeats;
   g) filtering the suspension of step (f) with a cell strainer to obtain a filtrate;
   h) centrifuging the filtrate to obtain a cell pellet; and
   i) dissolving the cell pellet with a nutrient medium to obtain the mesenchymal stem cell suspension, wherein the nutrient medium comprises 5% to 20% of a platelet lysate.

2. The method as claimed in claim 1, said method comprising:
   a) obtaining a bone marrow sample, wherein the bone marrow sample comprises clotted bone marrow;
   b) chopping the clotted bone marrow into pieces of at least 2 mm$^3$ to obtain chopped clotted bone marrow;
   c) contacting the chopped clotted bone marrow with at least one enzyme and at least one protein in the presence of a buffer to obtain a clotted bone marrow reaction solution, wherein the at least one protein is selected from the group consisting of heat shock proteins and combinations thereof;
   d) incubating the clotted bone marrow reaction solution at a temperature in a range of 35° C. to 39° C. for a time of at least 20 minutes at a speed in a range of 100 rpm to 200 rpm to obtain an incubated clotted bone marrow reaction solution;
   e) contacting the incubated clotted bone marrow reaction solution of step (d) with a growth medium to obtain a suspension;
   f) mixing the suspension for a plurality of repeats;
   g) filtering the suspension of step (f) with a cell strainer with a pore size in a range of 50 μm-100 μm to obtain a filtrate;
   h) centrifuging the filtrate at 1300 rpm to 1800 rpm for a time in a range of 10 minutes to 15 minutes to obtain a cell pellet; and
   i) dissolving the cell pellet with a nutrient medium to obtain the mesenchymal stem cell suspension, wherein the nutrient medium comprises 5% to 20% of a platelet lysate.

3. The method as claimed in claim 1, wherein the at least one enzyme is selected from the group consisting of urokinase, collagenase, hyaluronidase, and combinations thereof.

4. The method as claimed in claim 3, wherein urokinase is present in a range of 10,000 units to 30,000 units, collagenase type I-II is present in a range of 200 units to 500 units, hyaluronidase type I-IV is present in a range of 200 units to 1000 units, and the heat shock protein is HSP 70 present in a range of 100 ng/ml to 1 μg/ml.

5. The method as claimed in claim 1, wherein the growth medium is selected from a group consisting of a Minimum Essential Medium (α-MEM), Dulbecco's Modified Eagle Medium (DMEM), Iscove's Modified Dulbecco's Medium (IMDM), F12, Eagle's Minimum Essential Medium (EMEM), and combinations thereof.

6. The method as claimed in claim 1, wherein the nutrient medium comprises a medium selected from a group consisting of α-MEM, DMEM, IMDM, F12, EMEM and combinations thereof, and a plurality of factors selected from a group consisting of, Fibroblast Growth Factor (FGF), Transforming Growth Factor (TGF), Insulin-like Growth Factor 1 (IGF), Vascular Endothelial Growth Factor (VEGF), Platelet-derived Growth Factor (PDGF), Bone Morphogenic Protein-2 (BMP-2), and combinations thereof.

7. The method as claimed in claim 1, wherein the mesenchymal stem cell suspension comprises mesenchymal stem cells which are culture flask-adherent and stained with crystal violet stain.

8. The method as claimed in claim 1, wherein the mesenchymal stem cells test positive in flow cytometry cell surface marker analysis for CD90, CD73 and CD105, and negative for CD34 and HLA-DR.

9. The method as claimed in claim 1, wherein the platelet lysate comprises a lysate obtained from a mixture of an umbilical cord blood (UCB) derived platelet-rich plasma and a maternal blood (MB) derived platelet-rich plasma.

10. The method as claimed in claim 9, wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml.

11. The method of claim 1, further comprising:
j) seeding in a culture flask, the mesenchymal stem cell suspension obtained in step i), to obtain culture flask-adhered mesenchymal stem cells;
k) culturing the adhered mesenchymal stem cells in a nutrient medium comprising 5% to 20% of a platelet lysate in the nutrient medium;
l) supplementing the nutrient medium of step (k) with differentiation factors and growth factors to obtain a differentiation medium;
m) complementing the differentiation nutrient medium of step (l) with fresh differentiation nutrient medium comprising 5% to 20% of a platelet lysate, differentiation factors and growth factors to obtain a population of pre-osteoblast cells;
n) sub-culturing the population of pre-osteoblast cells of step (m) for a time in a range of 6 to 10 days to obtain a pre-osteoblast cells; and
o) expanding the pre-osteoblast cells in an expansion nutrient medium comprising 5% to 20% of a platelet lysate, for a time in a range of 10 to 20 days to obtain transplantation-ready osteoblast cells.

12. The method as claimed in claim 11, wherein the nutrient medium for culturing the adhered mesenchymal stem cells comprises a medium selected from a group consisting of α-MEM, DMEM, IMDM, F12, EMEM and combinations thereof; and a plurality of factors selected from a group consisting of FGF, TGF, VEGF, PDGF, IGF, BMP-2, and combinations thereof.

13. The method as claimed in claim 11, wherein the differentiation medium comprises a medium selected from a group consisting of α-MEM, DMEM, IMDM, F12, EMEM and combinations thereof; and a plurality of factors selected from a group consisting of FGF, TGF, IGF, VEGF, PDGF, BMP-2 L-Thyroxine, Calcitriol, Stanozolol, Dexamethasone, β-glycerophosphate, L-Ascorbic acid, and combinations thereof.

14. The method as claimed in claim 11, wherein the expansion medium comprises a medium selected from a group consisting of α-MEM, DMEM, IMDM, F12, EMEM and combinations thereof; and a plurality of factors selected from a group consisting of Genistein, FGF, TGF, IGF, VEGF, PDGF, BMP-2, and combinations thereof.

15. The method as claimed in claim 11, wherein the mesenchymal stem cells are culture flask-adherent and stain with crystal violet stain.

16. The method as claimed in claim 11, wherein the mesenchymal stem cells test positive in flow cytometry cell surface marker analysis for CD90, CD73 and CD105, and negative for CD34 and HLA-DR, wherein the mesenchymal stem cells test positive for OCT-4, Nanog, and Sox-2 markers in RT-PCR analysis, wherein the pre-osteoblast cells test positive in flow cytometry cell surface marker analysis for bone alkaline phosphatase (ALP), wherein the pre-osteoblast cells test positive in flow cytometry cell surface marker analysis for bone ALP, wherein the pre-osteoblast cells test positive for at least one marker selected from a group consisting of ALP, collagen-1, osterix, runx2, and ephrinB4 markers, and negative for Ephrin-b2 marker in RT-PCR analysis, and wherein the pre-osteoblast cells test positive for bone ALP by histochemical analysis.

17. The method as claimed in claim 11, wherein the transplantation-ready osteoblast cells test positive in flow cytometry cell surface marker analysis for ALP, wherein the transplantation-ready osteoblast cells test positive for alizarin red staining, and wherein the transplantation-ready osteoblast cells test positive for at least one marker selected from a group consisting of bone ALP, collagen-1, osterix, runx2 and ephrinB4 markers, and negative for Ephrin-b2 in RT-PCR analysis.

18. The method as claimed in claim 11, wherein the transplantation-ready osteoblast cells are in a range of $12 \times 10^6$ cells to $60 \times 10^6$ cells.

19. The method as claimed in claim 11, wherein the platelet lysate comprises a lysate obtained from a mixture of an umbilical cord blood (UCB) derived platelet-rich plasma and a maternal blood (MB) derived platelet-rich plasma.

20. The method as claimed in claim 19, wherein the mixture of an umbilical cord blood (UCB) derived platelet-rich plasma and a maternal blood (MB) derived platelet-rich plasma comprises $0.3 \times 10^9$ to $1.5 \times 10^9$ platelets/ml.

* * * * *

UNITED STATES PATENT AND TRADEMARK OFFICE
CERTIFICATE OF CORRECTION

PATENT NO. : 12,391,924 B2  
APPLICATION NO. : 17/428587  
DATED : August 19, 2025  
INVENTOR(S) : Satyen Sanghavi et al.

Page 1 of 1

It is certified that error appears in the above-identified patent and that said Letters Patent is hereby corrected as shown below:

In the Claims

Column 44, Claim 5, Line 38:
"a Minimum" should read: -- α Minimum --.

Signed and Sealed this
Twenty-first Day of October, 2025

John A. Squires
*Director of the United States Patent and Trademark Office*